US006635258B2

(12) United States Patent
Burke et al.

(10) Patent No.: US 6,635,258 B2
(45) Date of Patent: *Oct. 21, 2003

(54) HERPES SIMPLEX VIRUS VP22 VACCINES AND METHODS OF USE

(75) Inventors: Rae Lyn Burke, San Francisco, CA (US); Michael A. Tigges, Oakland, CA (US)

(73) Assignee: Chiron Corporation, Emeryville, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/084,669

(22) Filed: May 26, 1998

(65) Prior Publication Data

US 2003/0017174 A1 Jan. 23, 2003

Related U.S. Application Data

(60) Provisional application No. 60/047,359, filed on Jun. 2, 1997.

(51) Int. Cl.[7] .......................... A61K 39/00; A61K 39/12; A61K 39/245; A61K 39/255; A61K 39/265; A61K 39/27; C07K 1/00; C07K 14/00; C07K 17/00
(52) U.S. Cl. ................................. 424/231.1; 424/185.1; 424/204.1; 424/229.1; 530/350
(58) Field of Search ........................... 424/231.1, 204.1, 424/229.1, 235.1, 185.1; 530/826, 300, 350; 536/73.4, 23.72

(56) References Cited

U.S. PATENT DOCUMENTS 5,384,122 A * 1/1995 Cunningham ............ 424/231.1
5,714,152 A 2/1998 Burke et al.

FOREIGN PATENT DOCUMENTS

WO    WO 92/02251    2/1992
WO    WO 96/17072    6/1996
WO    WO 97/05265    2/1997

OTHER PUBLICATIONS

Elliot et al., Cell, vol. 88, pp. 223–233 (Jan. 1997).*
Barnett et al. Journal of General Virology, 73:2167–2171, 1992.*
Sequence Database SPTREMBL, accession P89468, May 1997.*
Bernstein et al., Vaccine 17:1681–1689, 1999.
Elliott et al., "The Herpes Simplex Virus Type 1 Tegument Protein VP22 is Encoded by Gene UL49," *Journal of General Virology* 73:723–726 (1992).
Elliott et al., "V16 Interacts Via Its Activation Domain with VP22, a Tegument Protein of Herpes Simples Virus, and is Relocated to a Novel Macromolecular Assembly in Coexpressing Cells," *Journal of Virology* 69(12):7932–7941(1995).
Koelle et al., "Antigenic Specificities of Human CD4+ T–Cell Clones Recovered from Recurrent Genital Herpes Simplex Virus Type 2 Lesions," *Journal of Virology* 68(5):2803–2810 (1994).
Leslie et al., "Overexpression of the Herpes Simplex Virus Type 1 Tegument Protein VP22 Increases Its Incorporation Into Virus Particles," *Virology* 220:60–68 (1996).
McGeoch et al., "The Complete DNA Sequence of the Long Unique Region in the Genome of Herpes Simplex Virus Type 1," *J. Gen. Virol.* 69:1531–1574 (1988).
Meredith et al., "Post–Translational Modification of the Tegument Proteins (VP13 and VP14) of Herpes Simplex Virus Type 1 by Glycosylation and Phosphorylation," *Journal of General Virology* 72:2771–2775 (1991).
Spear et al., "Proteins Specified by Herpes Simplex Virus," *Journal of Virology* 9(1):143–159 (1972).
Muggeridge et al., "Herpes simplex virus" in *Immunochemistry of viruses, II. The basis for serodiagnosis and vaccines.* Eds. M.H.V. van Regenmortel and A.R. Neurath, 1990 Elsevier Science Publishers B.V. (Biomedical Division) 1990.
Triezenberg et al., "Functional dissection of VP16, the trans–activator of herpes simplex virus immediate early gene expression," *Genes & Development* 2:718–729 (1998).

* cited by examiner

*Primary Examiner*—James Housel
*Assistant Examiner*—Zachariah Lucas
(74) *Attorney, Agent, or Firm*—Roberta L. Robins; Alisa A. Harbin; Robert P. Blackburn

(57) ABSTRACT

Vaccines containing herpes simplex virus (HSV) VP22 polypeptides capable of eliciting a cellular immune response and methods for treating and preventing HSV infections using the vaccines are disclosed. The vaccines can include additional HSV polypeptides, such as HSV glycoproteins. Also disclosed are methods of DNA immunization.

24 Claims, 5 Drawing Sheets

```
                MetThrSerArgArgSerValLysSerCysProArgGluAlaProArgGlyThr
  1 AGATCTATGACCTCTCGCCGCTCCGTCAAGTCGTGTCCGCGGGAAGCGCCGCGCGGGACC
    TCTAGATACTGGAGAGCGGCGAGGCAGTTCAGCACAGGCGCCCTTCGCGGCGCGCCCTGG

HisGluGluLeuTyrTyrGlyProValSerProAlaAspProGluSerProArgAspAsp
 61 CACGAGGAGTTGTACTATGGCCCGGTCTCCCCGGCGGACCCAGAGAGTCCGCGCGACGAC
    GTGCTCCTCAACATGATACCGGGCCAGAGGGGCCGCCTGGGTCTCTCAGGCGCGCTGCTG

PheArgArgGlyAlaGlyProMetArgAlaArgProArgGlyGluValArgPheLeuHis
121 TTCCGCCGCGGCGCTGGCCCGATGCGCGCGCGCCCGAGGGGCGAGGTTCGCTTTCTCCAT
    AAGGCGGCGCCGCGACCGGGCTACGCGCGCGCGGGCTCCCCGCTCCAAGCGAAAGAGGTA

TyrAspGluAlaGlyTyrAlaLeuTyrArgAspSerSerSerAspAspAspGluSerArg
181 TATGACGAGGCTGGGTATGCCCTCTACCGGGACTCGTCTTCGGACGACGACGAGTCCCGG
    ATACTGCTCCGACCCATACGGGAGATGGCCCTGAGCAGAAGCCTGCTGCTGCTCAGGGCC

AspThrAlaArgProArgArgSerAlaSerValAlaGlySerHisGlyProGlyProAla
241 GATACCGCGCGACCGCGTCGTTCGGCGTCCGTCGCGGGCTCTCACGGCCCCGGCCCCGCG
    CTATGGCGCGCTGGCGCAGCAAGCCGCAGGCAGCGCCCGAGAGTGCCGGGGCCGGGGCGC

ArgAlaProProProProGlyGlyProValGlyAlaGlyGlyArgSerHisAlaProPro
301 CGCGCTCCTCCACCCCCGGGGGCCCCGTGGGCGCCGGCGGGCGCTCGCACGCCCCTCCC
    GCGCGAGGAGGTGGGGGGCCCCGGGGCACCCGCGGCCGCCCGCGAGCGTGCGGGGAGGG

AlaArgThrProLysMetThrArgGlyAlaProLysAlaSerAlaThrProAlaThrAsp
361 GCGCGGACCCCCAAAATGACGCGCGGGGCGCCTAAGGCCTCCGCGACCCCGGCGACCGAC
    CGCGCCTGGGGGTTTTACTGCGCGCCCCGCGGATTCCGGAGGCGCTGGGGCCGCTGGCTG

ProAlaArgGlyArgArgProAlaGlnAlaAspSerAlaValLeuLeuAspAlaProAla
421 CCCGCCCGCGGCAGGCGACCCGCCCAGGCCGACTCCGCCGTGCTCCTAGACGCCCCCGCT
    GGGCGGGCGCCGTCCGCTGGGCGGGTCCGGCTGAGGCGGCACGAGGATCTGCGGGGGCGA
```

*FIG. 1A*

```
        ProThrAlaSerGlyArgThrLysThrProAlaGlnGlyLeuAlaLysLysLeuHisPhe
481  CCCACGGCCTCGGGAAGAACCAAGACACCCGCCCAGGGACTGGCCAAGAAGCTGCACTTC
     GGGTGCCGGAGCCCTTCTTGGTTCTGTGGGCGGGTCCCTGACCGGTTCTTCGACGTGAAG

SerThrAlaProProSerProThrAlaProTrpThrProArgValAlaGlyPheAsnLys
541  AGCACCGCCCCACCGAGCCCCACGGCGCCGTGGACCCCCCGGGTGGCCGGGTTCAACAAG
     TCGTGGCGGGGTGGCTCGGGGTGCCGCGGCACCTGGGGGGCCCACCGGCCCAAGTTGTTC

ArgValPheCysAlaAlaValGlyArgLeuAlaAlaThrHisAlaArgLeuAlaAlaVal
601  CGCGTCTTCTGCGCCGCGGTCGGGCGCCTGGCGGCCACGCACGCCCGGCTGGCGGCGGTA
     GCGCAGAAGACGCGGCGCCAGCCCGCGGACCGCCGGTGCGTGCGGGCCGACCGCCGCCAT

GlnLeuTrpAspMetSerArgProHisThrAspGluAspLeuAsnGluLeuLeuAspLeu
661  CAGCTGTGGGACATGTCGCGGCCGCACACCGACGAAGACCTCAACGAGCTCCTCGACCTC
     GTCGACACCCTGTACAGCGCCGGCGTGTGGCTGCTTCTGGAGTTGCTCGAGGAGCTGGAG

ThrThrIleArgValThrValCysGluGlyLysAsnLeuLeuGlnArgAlaAsnGluLeu
721  ACCACCATTCGCGTGACGGTCTGCGAGGGCAAGAACCTCCTGCAGCGCGCGAACGAGTTG
     TGGTGGTAAGCGCACTGCCAGACGCTCCCGTTCTTGGAGGACGTCGCGCGCTTGCTCAAC

ValAsnProAspAlaAlaGlnAspValAspAlaThrAlaAlaAlaArgGlyArgProAla
781  GTGAATCCCGACGCGGCGCAGGACGTCGACGCGACCGCGGCCGCCCGGGGCCGCCCCGCG
     CACTTAGGGCTGCGCCGCGTCCTGCAGCTGCGCTGGCGCCGGCGGGCCCCGGCGGGGCGC

GlyArgAlaAlaAlaThrAlaArgAlaProAlaArgSerAlaSerArgProArgArgPro
841  GGGCGTGCCGCCGCGACCGCACGGGCCCCCGCCCGCTCGGCTTCCCGTCCCCGCCGCCCC
     CCCGCACGGCGGCGCTGGCGTGCCCGGGGCGGGCGAGCCGAAGGGCAGGGGCGGCGGGG

LeuGluGluTyrMetProMetGluAM
901  CTCGAGGAATACATGCCAATGGAATAGAGATCT
     GAGCTCCTTATGTACGGTTACCTTATCTCTAGA
```

*FIG. 1B*

SEQUENCE LISTING

<160> NUMBER OF SEQ ID NOS: 5

<210> SEQ ID NO 1
<211> LENGTH: 933
<212> TYPE: DNA
<213> ORGANISM: Herpes Simplex Virus-2
<220> FEATURE:
<221> NAME/KEY: CDS
<222> LOCATION: (7)..(924)

<400> SEQUENCE: 1

```
agatct atg acc tct cgc cgc tcc gtc aag tcg tgt ccg cgg gaa gcg          48
       Met Thr Ser Arg Arg Ser Val Lys Ser Cys Pro Arg Glu Ala
        1               5                  10 ccg cgc ggg acc cac gag gag ttg tac tat ggc ccg gtc tcc ccg gcg         96
Pro Arg Gly Thr His Glu Glu Leu Tyr Tyr Gly Pro Val Ser Pro Ala
 15                  20                  25                  30 gac cca gag agt ccg cgc gac gac ttc cgc cgc ggc gct ggc ccg atg        144
Asp Pro Glu Ser Pro Arg Asp Asp Phe Arg Arg Gly Ala Gly Pro Met
                 35                  40                  45 cgc gcg cgc ccg agg ggc gag gtt cgc ttt ctc cat tat gac gag gct        192
Arg Ala Arg Pro Arg Gly Glu Val Arg Phe Leu His Tyr Asp Glu Ala
             50                  55                  60 ggg tat gcc ctc tac cgg gac tcg tct tcg gac gac gac gag tcc cgg        240
Gly Tyr Ala Leu Tyr Arg Asp Ser Ser Ser Asp Asp Asp Glu Ser Arg
         65                  70                  75 gat acc gcg cga ccg cgt cgt tcg gcg tcc gtc gcg ggc tct cac ggc        288
Asp Thr Ala Arg Pro Arg Arg Ser Ala Ser Val Ala Gly Ser His Gly
     80                  85                  90 ccc ggc ccc gcg cgc gct cct cca ccc ccc ggg ggc ccc gtg ggc gcc        336
Pro Gly Pro Ala Arg Ala Pro Pro Pro Pro Gly Gly Pro Val Gly Ala
 95                 100                 105                 110 ggc ggg cgc tcg cac gcc cct ccc gcg cgg acc ccc aaa atg acg cgc        384
Gly Gly Arg Ser His Ala Pro Pro Ala Arg Thr Pro Lys Met Thr Arg
                115                 120                 125 ggg gcg cct aag ggc tcc gcg acc ccg gcg acc gac ccc gcc cgc ggc        432
Gly Ala Pro Lys Gly Ser Ala Thr Pro Ala Thr Asp Pro Ala Arg Gly
            130                 135                 140 agg cga ccc gcc cag gcc gac tcc gcc gtg ctc cta gac gcc ccc gct        480
Arg Arg Pro Ala Gln Ala Asp Ser Ala Val Leu Leu Asp Ala Pro Ala
        145                 150                 155 ccc acg gcc tcg gga aga acc aag aca ccc gcc cag gga ctg gcc aag        528
Pro Thr Ala Ser Gly Arg Thr Lys Thr Pro Ala Gln Gly Leu Ala Lys
    160                 165                 170 aag ctg cac ttc agc acc gcc cca ccg agc ccc acg gcg ccg tgg acc        576
Lys Leu His Phe Ser Thr Ala Pro Pro Ser Pro Thr Ala Pro Trp Thr
175                 180                 185                 190 ccc cgg gtg gcc ggg ttc aac aag cgc gtc ttc tgc gcc gcg gtc ggg        624
Pro Arg Val Ala Gly Phe Asn Lys Arg Val Phe Cys Ala Ala Val Gly
                195                 200                 205 cgc ctg gcg gcc acg cac gcc cgg ctg gcg gcg gta cag ctg tgg gac        672
Arg Leu Ala Ala Thr His Ala Arg Leu Ala Ala Val Gln Leu Trp Asp
            210                 215                 220 atg tcg cgg ccg cac acc cac gaa gac ctc aac gag ctc ctc gac ctc        720
Met Ser Arg Pro His Thr His Glu Asp Leu Asn Glu Leu Leu Asp Leu
        225                 230                 235 acc acc att cgc gtg acg gtc tgc gag ggc aag aac ctc ctg cag cgc        768
Thr Thr Ile Arg Val Thr Val Cys Glu Gly Lys Asn Leu Leu Gln Arg
    240                 245                 250
```

```
gcg aac gag ttg gtg aat ccc gac gcg gcg cag gac gtc gac gcg acc        816
Ala Asn Glu Leu Val Asn Pro Asp Ala Ala Gln Asp Val Asp Ala Thr
255                 260                 265                 270 gcg gcc gcc cgg ggc cgc ccc gcg ggg cgt gcc gcc gcg acc gca cgg        864
Ala Ala Ala Arg Gly Arg Pro Ala Gly Arg Ala Ala Ala Thr Ala Arg
                275                 280                 285 gcc ccc gcc cgc tcg gct tcc cgt ccc cgc cgc ccc ctc gag gaa tac        912
Ala Pro Ala Arg Ser Ala Ser Arg Pro Arg Arg Pro Leu Glu Glu Tyr
                290                 295                 300 atg cca atg gaa tagagatct                                              933
Met Pro Met Glu
            305

<210> SEQ ID NO 2
<211> LENGTH: 306
<212> TYPE: PRT
<213> ORGANISM: Herpes Simplex Virus-2

<400> SEQUENCE: 2

Met Thr Ser Arg Arg Ser Val Lys Ser Cys Pro Arg Glu Ala Pro Arg
 1               5                  10                  15

Gly Thr His Glu Glu Leu Tyr Tyr Gly Pro Val Ser Pro Ala Asp Pro
                20                  25                  30

Glu Ser Pro Arg Asp Asp Phe Arg Arg Gly Ala Gly Pro Met Arg Ala
            35                  40                  45

Arg Pro Arg Gly Glu Val Arg Phe Leu His Tyr Asp Glu Ala Gly Tyr
        50                  55                  60

Ala Leu Tyr Arg Asp Ser Ser Asp Asp Glu Ser Arg Asp Thr
 65                 70                  75                  80

Ala Arg Pro Arg Arg Ser Ala Ser Val Ala Gly Ser His Gly Pro Gly
                85                  90                  95

Pro Ala Arg Ala Pro Pro Pro Gly Gly Pro Val Gly Ala Gly Gly
            100                 105                 110

Arg Ser His Ala Pro Pro Ala Arg Thr Pro Lys Met Thr Arg Gly Ala
        115                 120                 125

Pro Lys Gly Ser Ala Thr Pro Ala Thr Asp Pro Ala Arg Gly Arg Arg
    130                 135                 140

Pro Ala Gln Ala Asp Ser Ala Val Leu Leu Asp Ala Pro Ala Pro Thr
145                 150                 155                 160

Ala Ser Gly Arg Thr Lys Thr Pro Ala Gln Gly Leu Ala Lys Lys Leu
                165                 170                 175

His Phe Ser Thr Ala Pro Pro Ser Pro Thr Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Thr His Ala Arg Leu Ala Ala Val Gln Leu Trp Asp Met Ser
    210                 215                 220

Arg Pro His Thr His Glu Asp Leu Asn Glu Leu Leu Asp Leu Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Ala Ala Gln Asp Val Asp Ala Thr Ala Ala
            260                 265                 270

Ala Arg Gly Arg Pro Ala Gly Arg Ala Ala Thr Ala Arg Ala Pro
        275                 280                 285

Ala Arg Ser Ala Ser Arg Pro Arg Arg Pro Leu Glu Glu Tyr Met Pro
```

```
                  290                 295                 300
Met Glu
305

<210> SEQ ID NO 3
<211> LENGTH: 98
<212> TYPE: DNA
<213> ORGANISM: Artificial Sequence
<220> FEATURE:
<223> OTHER INFORMATION: Description of Artificial Sequence: cloning
      site in vector pAc13

<400> SEQUENCE: 3
tataaatatt ccgggcgcgg atcggtacca gatctgcaga attctagagg atcctgatca        60
gctagcagag ctcgcggccg cccgggccgt accgactc                               98

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 4
ggtaccagat ctatgacctc tcgccgc                                           27

<210> SEQ ID NO 5
<211> LENGTH: 55
<212> TYPE: DNA
<213> ORGANISM: Artificial Sequence
<220> FEATURE:
<223> OTHER INFORMATION: Description of Artificial Sequence: PCR primer

<400> SEQUENCE: 5
ctctgcagat ctctattcca ttggcatgta ttcctcgagg gggcggcggg gagcg            55
```

HERPES SIMPLEX VIRUS VP22 VACCINES AND METHODS OF USE

CROSS-REFERENCE TO RELATED APPLICATIONS

This application is related to provisional patent application Ser. No. 60/047,359, filed Jun. 2, 1997, from which priority is claimed under 35 USC §119(e) (1) and which application is incorporated herein by reference in its entirety.

BACKGROUND OF THE INVENTION

1. Technical Field

The present invention relates generally to herpesvirus vaccine compositions. In particular, the invention pertains to vaccines containing VP22 polypeptides and methods for treating and preventing herpes simplex virus infections using the vaccines.

2. Background of the Invention

Herpes simplex virus (HSV) infections are extremely prevalent and have a range of manifestations from apparently asymptomatic acquisition to severe disease and life-threatening infections in the immunocompromised individual and the neonate. These infections are caused by two viruses, herpes simplex virus type 1 (HSV-1) and herpes simplex virus type 2 (HSV-2). HSV-1 is the predominant cause of oral infections and is usually acquired in childhood, whereas HSV-2 infections are usually sexually transmitted genital infections. These distinctions are blurred, however, and up to 25% of genital herpes is caused by HSV-1. Following initial infection, the virus establishes a life-long latent state and periodically reactivates, causing clinically apparent lesional episodes or asymptomatic virus shedding.

Despite the availability of the antiviral agent, acyclovir, the incidence of HSV-2 in the population ranges from 8–50% and is increasing. The apparent reason for this increase is that most individuals are unaware of their infection. Moreover, the majority of transmission occurs from virus shed asymptomatically.

In general, HSV is a double-stranded DNA virus having a genome of about 150–160 kbp. The viral genomes of HSV-1 and HSV-2 are colinear and share greater than 50% homology over the entire genome. For some genes, the amino acid identity between the two virus types is as much as 80 to 90%. As a result of this similarity, many HSV-specific antibodies are cross-reactive for both virus types.

The viral genome is packaged within an icosahedral nucleocapsid which is enveloped in a membrane. The membrane (or envelope) includes at least 10 virus-encoded glycoproteins, the most abundant of which are gB, gC, gD, and gE. The viral glycoproteins are involved in the processes of virus attachment to cellular receptors and in fusion of the viral and host cell membranes to permit virus entry into the cell. As a consequence of their location (on the surface of the virion) and their role, the glycoproteins are targets of neutralizing antibody and antibody dependent cell cytotoxicity (ADCC) antibody. Within a virus type, there is a limited (1 to 2%) strain-to-strain sequence variability of the glycoprotein genes. The viral genome also encodes over 70 other proteins, including VP16 and VP22 which are associated with the virion tegument, located between the capsid and the envelope. (VP stands for "virion protein.")

One approach to HSV vaccine development has been the use of isolated glycoproteins which have been shown to be both protective and therapeutic. See, e.g., Burke et al., *Virology* (1991) 181:793–797; Burke et al., *Rev. Infect. Dis.* (1991) 13(Suppl 11):S906–S911; Straus et al., *Lancet* (1994) 343:1460–1463; Ho et al., *J. Virol.* (1989) 63:2951–2958; Stanberry et al., *J. Infect. Dis.* (1988) 157:156–163; and Stanberry et al., (1987) *J. Infect. Dis.* 155:914–920; Stanberry, L. R. "Subunit Viral Vaccines: prophylactic and therapeutic use." In: Aurelian L (ed.) *Herpesviruses, the Immune Systems and Aids.* Kluwer, Boston, pp. 309–341. Similarly, the use of VP16 in vaccine compositions has recently been described. See, EP Publication No. 541,692. In addition, T-cell clones recovered from herpetic lesions have been shown to be reactive with VP16 (see, Koelle et al., *J. Virol.* (1994) 68:2803–2810).

There is growing evidence that vaccination against a number of viruses should target both the cellular and humoral arms of the immune system. In this regard, cytotoxic T-lymphocytes (CTLs) play an important role in cell-mediated immune defense against intracellular pathogens and in particular against viruses. CTLs mediate cytotoxicity of virally infected cells by recognizing viral determinants in conjunction with class I MHC molecules displayed by the infected cells. Cytoplasmic expression of proteins is generally considered to be a prerequisite for class I MHC processing and presentation of antigenic peptides to CTLs. Immunization with subunit glycoprotein vaccines may fail to effectively produce the CTLs necessary to curb intracellular infection.

Accordingly, the wide spread availability of an efficacious vaccine against HSV, able to elicit a cellular immune response, would therefore be highly desirable.

SUMMARY OF THE INVENTION

The present invention provides a method for treating and preventing HSV infection, as well as compositions for use in the method. In particular, the compositions include polypeptides derived from the viral tegument protein VP22 which, as shown herein, are able to elicit a cellular immune response. The compositions can include additional HSV polypeptides, such as HSV glycoproteins and VP16. In this way, immunization will elicit both cellular and humoral immunity and provide an extremely efficacious method for protecting against and treating HSV infection.

Accordingly, in one embodiment, the subject invention is directed to a subunit vaccine composition comprising a HSV VP22 polypeptide which is capable of eliciting a cellular immune response in a mammalian subject, and a pharmaceutically acceptable excipient. The VP22 polypeptide may be derived from HSV-1 or HSV-2. Alternative embodiments are directed to compositions which additionally comprise HSV VP16 polypeptides and/or HSV glycoproteins.

In another embodiment, the invention is directed to a method of producing a composition for the treatment or prevention of HSV infection comprising:

(a) providing an isolated VP22 polypeptide which is capable of eliciting a cellular immune response in a mammalian subject; and (b) formulating the VP22 polypeptide with a pharmaceutically acceptable excipient.

In yet another embodiment, the subject invention is directed to a method for treating or preventing HSV infection in a mammalian subject comprising administering a composition as described above, to the subject. The composition can be administered prior to, and/or subsequent to, primary infection.

In a further embodiment, the invention is directed to a viral vector comprising a gene encoding a HSV VP22 polypeptide capable of eliciting a cellular immune response in a mammalian subject. The gene may be derived from HSV-1 or HSV-2.

In yet another embodiment, the subject invention is directed to a method for treating or preventing HSV infection in a mammalian subject comprising administering a viral vector as described above, to the subject.

In still a further embodiment, the invention is directed to a vaccine composition comprising a recombinant vector which comprises a gene encoding a HSV VP22 polypeptide operably linked to control elements that direct the transcription and translation of the gene in a mammalian host cell, and a pharmaceutically acceptable excipient. The gene encoding the VP22 polypeptide may be derived from HSV-1 or HSV-2 and the vector can be a nonviral or a viral vector.

In yet another embodiment, the subject invention is directed to a method for treating or preventing HSV infection in a mammalian subject comprising administering the composition above.

These and other embodiments of the present invention will readily occur to those of ordinary skill in the art in view of the disclosure herein.

BRIEF DESCRIPTION OF THE FIGURES

FIGS. 1A–1B (SEQ ID NOS:1–2) depict the sequence of the UL49 ORF and the predicted amino acid sequence of HSV-2 VP22. The conservative C→T base change is underlined at position 70.

DETAILED DESCRIPTION OF THE INVENTION

Figure 2:
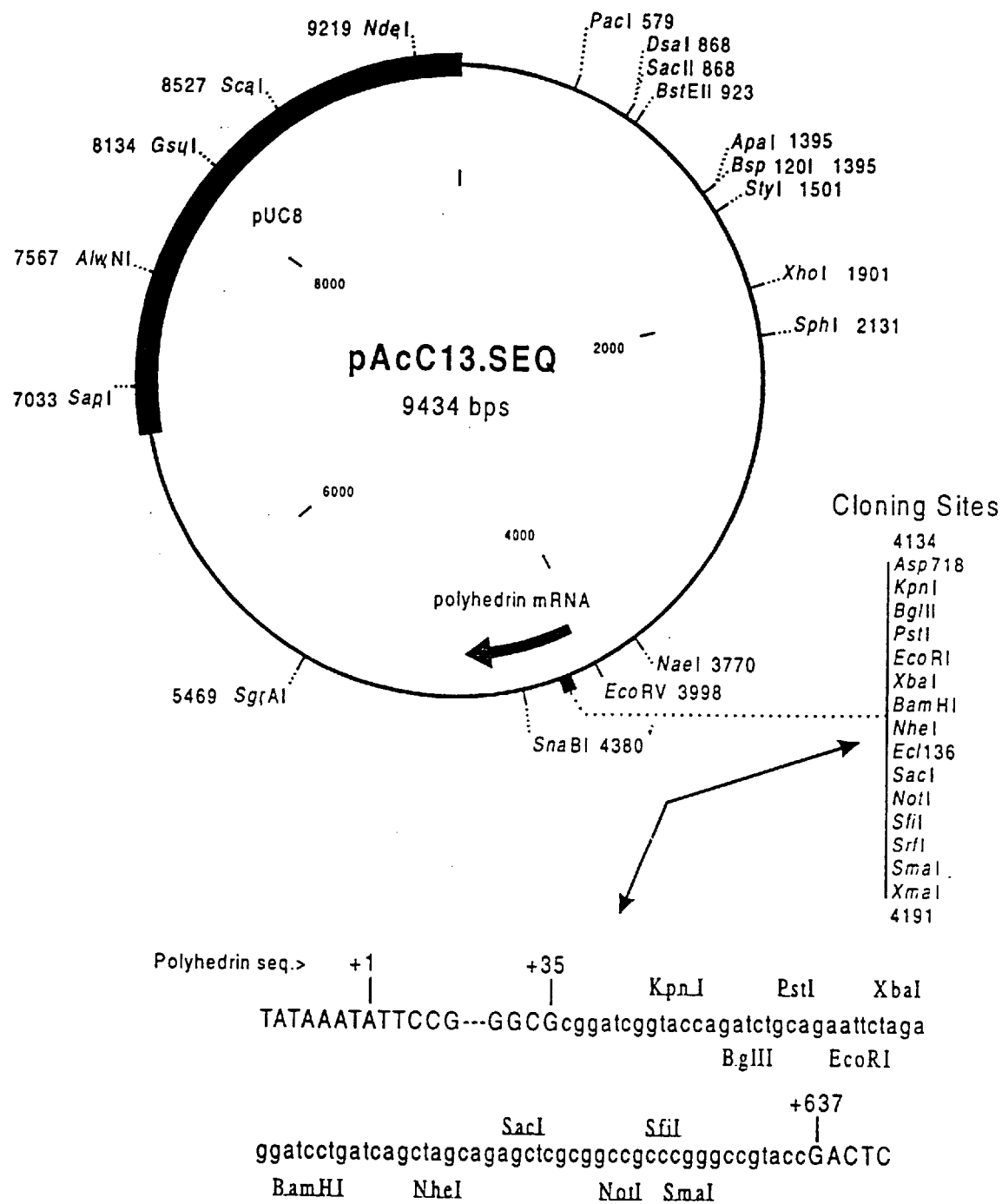
FIG. 2 SEQ ID NO: 3 depicts a baculovirus expression vector, pAc13, which contains the nucleotide sequence encoding VP22.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al., *Molecular Cloning: A Laboratory Manual* (2nd Edition, 1989); *DNA Cloning: A Practical Approach,* vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984); *Fundamental Virology,* 2nd Edition, vol. I & II (B. N. Fields and D. M. Knipe, eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

I. Definitions

In describing the present invention, the following terms will be employed, and are intended to be defined as indicated below.

The term "polypeptide" when used with reference to HSV VP22, VP16, gB, gD, etc., refers to a VP22, VP16, gB, gD, etc., polypeptide, whether native, recombinant or synthetic, derived from any of the various HSV-1 or HSV-2 strains. The term intends polypeptides derived from any of the various HSV proteins, including glycoproteins, tegument proteins etc. The polypeptide need not include the full-length amino acid sequence of the reference molecule but need only include so much of the molecule as necessary in order for the polypeptide to function for its intended purpose. Thus, for example, in the case of VP22, one or more epitopes capable of eliciting a cellular immune response, as defined below, need be present.

Accordingly, the polypeptide may comprise the full-length sequence, fragments, truncated and partial sequences, analogs, and precursor forms of the reference molecule, as well as fusions of the polypeptide with other proteins. The term therefore intends deletions, additions and substitutions to the sequence, so long as the polypeptide functions as intended. In this regard, particularly preferred substitutions will generally be conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. Proteins having substantially the same amino acid sequence as the reference molecule, but possessing minor amino acid substitutions that do not substantially affect the antibody binding capabilities of the protein, are therefore within the definition of the reference polypeptide.

The term "HSV glycoprotein" refers to a polypeptide as defined above which is derived from any of the glycoproteins found in the membrane region of HSV-1 and HSV-2. Presently preferred HSV glycoproteins are gB, gC, gD and gE, derived from either of HSV-1 or HSV-2. Included in the definition are glycoproteins extracted from natural sources (e.g., from infected cell culture) and glycoproteins produced synthetically or recombinantly. Such glycoproteins may be modified, either by chemical or enzymatic means (e.g., proteolytic cleavage, deglycosylation, etc.) or by mutation, or by recombinant DNA techniques (e.g., fusing genes coding for HSV glycoprotein epitopes with each other or with other genes to provide fusion proteins, or by deleting or replacing sections of the DNA sequence).

For example, it may be desirable to delete all or part of the transmembrane domain and cytoplasmic domain present in the molecule. See, e.g., International Publication Nos. WO 96/04382, published Feb. 15, 1996 and WO 95/31555, published Nov. 23, 1995. Such deletions allow for enhanced secretion and solubility, and hence increased recovery of the molecules when produced recombinantly, while still maintaining reactivity with antibodies to HSV-1 and/or HSV-2. The location of a transmembrane domain in a given protein can be determined using a computer program that formulates a hydropathy scale from the amino acid sequence of the protein, utilizing the hydrophobic and hydrophilic properties of each of the 20 amino acids, as described in, e.g., Kyte et al., *J. Mol. Biol.* (1982) 157:105–132; and Hopp and Woods, *Proc. Natl. Acad. Sci. USA* (1981) 78:3824–3828. HSV gB and gD and antigenic portions thereof are described further below.

By "VP22 polypeptide" is meant a polypeptide as defined above, which is derived from HSV-1 or HSV-2 VP22. VP22 is a viral tegument protein, located between the capsid and the envelope of the virus. The gene encoding VP22 is designated "UL49" (open reading frame 49 in the unique long segment of the HSV genome). See, e.g., Elliott and Meredith, *J. Gen. Virol.* (1992) 73:723–726. The DNA sequence of HSV-1 UL49 and the amino acid sequence of HSV-1 VP22 have been reported. See, e.g., McGeoch et al., *J. Gen. Virol.* (1988) 69:1531–1574. The DNA and corresponding amino acid sequences of HSV-2 VP22 are shown in FIGS. 1A–1B (SEQ ID NOS:1–2) herein. The sequence depicted in FIGS. 1A–1B has one conservative base change (C->T leu->leu) at position 70 as compared to a reference HSV-2. The term "VP22" includes substitutions, deletions and additions to the reference sequence, as described above, so long as the molecule retains its ability to elicit a cellular immune response. HSV-1 and HSV-2 VP22 include 301 and 300 amino acids, respectively. The two proteins share approximately 68.9% homology.

By "VP16 polypeptide" is meant a polypeptide as defined above, which is derived from HSV-1 or HSV-2 VP16. VP16 is a viral tegument protein, located between the capsid and the envelope of the virus, and is also known as ICP25, VmW65 and the α-trans-inducing factor (αTIF). The DNA and amino acid sequences of HSV-1 VP16 have been reported. See, e.g., Campbell et al., *J. Mol. Biol.* (1984) 180:1; and Triezenberg et al., *Genes and Develop.* (1988) 2:718. Similarly, the DNA and corresponding amino acid sequences of HSV-2 VP16 are known. See, e.g., EP Publication No. 541,692. HSV-1 and HSV-2 VP16 include 489 amino acids. The two proteins share approximately 85% homology. A representative truncated derivative of VP16 for use herein includes a VP16 polypeptide having amino acids 1–416. This, as well as other VP16 polypeptides, which are capable of eliciting a cellular immune response, will find use with the present methods.

By "gB polypeptide" is meant a polypeptide as defined above which is derived from HSV-1 gB (gB1) or HSV-2 gB (gB2). The DNA and corresponding amino acid sequences for gB1 and gB2 derived from various strains of HSV are known and reported in, e.g., U.S. Pat. Nos. 5,244,792 and 4,642,333; PCT Publication No. WO88/02634, published Apr. 21, 1988; Stuve et al., *J. Virol.* (1987) 61:326–335; Pellett et al., *J. Virol.* (1985) 53:243–253; and Bzik et al., *Virology* (1984) 133:301–314. The full-length, precursor gB1 protein includes about 904 amino acids of which about 1 to 30 comprise the first hydrophobic region which includes the signal sequence; 31 to about 726 comprise a region of variable polarity; amino acids 727 to about 795 comprise the second hydrophobic region which includes the transmembrane anchor; and amino acids 796 to about 904 constitute the second variable polarity region which includes the cytoplasmic domain. Similarly, the full-length gB2 protein is about 904 amino acids in length. The first 22 amino acids constitute a signal sequence and the mature, non-glycosylated protein, after cleavage of this sequence, has a predicted molecular weight of about 98 kD. Amino acids 23 to about 723 constitute the first region of variable polarity; amino acids 724 to about 798 comprise the transmembrane domain; and amino acids 799 to about 904 constitute the second variable polarity region which includes the cytoplasmic domain.

Representative truncated derivatives of gB, lacking all or a portion of the transmembrane domain and cytoplasmic domain, are described in, e.g., U.S. Pat. No. 5,244,792 (see, e.g., the description of plasmid pHS114 (ATCC Accession No. 39651), which contains a gB1 gene lacking 580 bp from the 3'-end of the gene and encoding a protein lacking the 194-carboxyl terminal amino acids; and plasmid pHS210 which includes a gB2 gene lacking 637 bp from the 3'-end). U.S. Pat. No. 5,171,568 describes plasmid pHS127A (ATCC Accession No. 39652), having a 1187 base pair gB1 gene fragment. Any of these derivatives, as well as others, which are capable of eliciting an immunological response, will find use in the present compositions and methods.

By "gD polypeptide" is meant a polypeptide as defined above which is derived from HSV-1 gD (gD1) or HSV-2 gD (gD2). The DNA and corresponding amino acid sequences for gD1 and gD2 are known. See, e.g., U.S. Pat. Nos. 4,818,694 and 4,855,224; Lasky and Dowbenko, *DNA* (1984) 3:23–29; Watson et al., *Gene* (1983) 26:307–312; and Watson et al., *Science* (1982) 218:381–384. The gD1 and gD2 proteins share about 86% homology overall. Full-length gD1 and gD2 both include about 393 amino acids with transmembrane domains at residues 333–362 and cytoplasmic domains extending to the carboxy-terminus at residue 393 The gD1 and gD2 proteins have signal sequences occurring at positions 1 through 25.

Representative truncated derivatives of gD, lacking all or a portion of the transmembrane and cytoplasmic domains, have been described in U.S. Pat. No. 5,171,568 (see, e.g., the description of plasmids pHS211 and pHS213, including gD2 genes encoding the first 305 amino acids and the first 352 amino acids, respectively, of gD2; and the description of plasmid pHS132, including a gD1 gene encoding 315 amino acids of gD1); Lasky et al., *Bio/Technology* (June 1984) :527–532 (describing a truncated gD1 gene which encodes for a gD1 polypeptide having the first 300 amino acid residues). Various gD polypeptides have also been constructed which lack all or part of the signal sequence as described in U.S. Pat. No. 4,618,578 (see, e.g., the description of plasmids pYHS116 and pYHS117, which include a 600 bp 5'-deletion that includes deletion of the signal sequence coding region of gD1; plasmid pYHS118, which includes the 600 bp deletion above, as well as a 1300 bp deletion in the 3'-end of the coding region which includes most of the anchor sequence of gD1; plasmid pYHS119 which includes the 600 bp deletion to the 5'-end and a 2400 bp deletion in the 3'-end which includes deletion of the entire membrane anchor region and about 700 bp upstream of the anchor sequence of gD1). Any of these derivatives, as well as others, which are capable of eliciting an immunological response, will find use in the present compositions and methods.

By "epitope" is meant a site on an antigen to which specific B cells and T cells respond. The term is also used interchangeably with "antigenic determinant" or "antigenic determinant site." The term "epitope" as used herein refers to both linear and conformation epitopes. An epitope can comprise 3 or more amino acids in a spatial conformation unique to the epitope. Generally, an epitope consists of at least 5 such amino acids and, more usually, consists of at least 8–10 such amino acids. The identification of epitopes in a given protein is readily accomplished using techniques well known in the art. For example, methods of determining spatial conformation of amino acids are known in the art and include, e.g., x-ray crystallography and 2-dimensional nuclear magnetic resonance. See, e.g., *Epitope Mapping Protocols in Methods in Molecular Biology*, Vol. 66 (Glenn E. Morris, Ed., 1996). Other methods for determining epitopes are also known. See, e.g., Geysen et al., *Proc. Natl. Acad. Sci. USA* (1984) 81:3998–4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709–715 (technique for identifying peptides with high affinity for a given antibody). Antibodies that recognize the same epitope can be identified in a simple immunoassay showing the ability of one antibody to block the binding of another antibody to a target antigen.

An "immunological response" to a composition or vaccine, as used herein, is the development in the subject of a humoral and/or a cellular immune response to the polypeptides present in the vaccine of interest. A "cellular immune response" for purposes of the present invention will be one which serves to sensitize a mammalian subject by the presentation of the antigen of interest at the cell surface, in association with class I or class II MHC molecules. In this way, CTLs can be generated against the presented molecule to allow for the future protection of an immunized host. The presence of a cell-mediated immunological response may be determined using CTL cytotoxic cell assays, well known in the art, such as the assay described in Erickson et al. *J. Immunol.* (1993) 151:4189–4199; Doe et al. *Eur. J. Immunol.* (1994) 24:2369–2376 and described further below in the examples.

Polypeptides in the compositions of the present invention may also elicit an antibody-mediated, or humoral, immune response. Thus, an immunological response as used herein will be one which stimulates the production of CTLs and may also include one or more of the following effects; the production of antibodies by B cells, helper T cells and suppressor T cells, directed specifically to an antigen or antigens present in the composition or vaccine of interest. These responses may serve to neutralize infectivity, and/or mediate antibody-complement or antibody dependent cell cytotoxicity to provide protection to an immunized host. Such responses can be determined using standard immunoassays and neutralization assays, well known in the art, such as Western blots, dot blots and immunoaffinity assays.

By "subunit vaccine" is meant a vaccine composition which includes one or more selected immunogenic polypeptides but not all polypeptides, derived from or homologous to an antigen from HSV. Such a composition is substantially free of intact pathogen cells or particles, or the lysate of such cells or particles. Thus, a "subunit vaccine" can be prepared from at least partially purified (preferably substantially purified) immunogenic polypeptides from HSV, or analogs thereof. The method of obtaining an antigen included in the subunit vaccine can thus include standard purification techniques, recombinant production, or synthetic production.

Two nucleic acid or polypeptide sequences are "substantially homologous" when at least about 70%, preferably at least about 80–90%, and most preferably at least about 95% or more, of the nucleotides or amino acids match over a defined length of the molecule. As used herein, substantially homologous also refers to sequences showing identity to the specified nucleic acid or polypeptide sequence. Nucleic acid sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning,* vols I & II, supra; *Nucleic Acid Hybridization,* supra. Such sequences can also be confirmed and further characterized by direct sequencing of PCR products. For example, homology can be determined by hybridization of polynucleotides under conditions which form stable duplexes between homologous regions. Stable duplexes are those, for example, which withstand digestion with a single-stranded specific nuclease(s), such as S1. Such duplexes can be analyzed by various methods, such as size determination of digested fragments.

"Stringency" refers to conditions in a hybridization reaction that favor association of very similar sequences over sequences that differ. For example, the combination of temperature and salt concentration should be chosen that is approximately 12 to 20 degrees C. below the calculated Tm of the hybrid under study.

Other techniques for determining sequence identity are well known in the art and include determining the sequence of the polynucleotide or polypeptide of interest and comparing this to a second sequence. Programs available in the Wisconsin Sequence Analysis Package, Version 8 (available from Genetics Computer Group, Madison, Wis.) for example, the BESTFIT, FASTA and GAP programs, are capable of calculating identity between two molecules.

A "purified" or "isolated" polypeptide is a polypeptide which is recombinantly or synthetically produced, or isolated from its natural source, such that the amount of protein present in a composition is substantially higher than that present in a crude viral preparation. In general, a purified protein would be >50% homogeneous and more preferably >80–90% homogeneous. Some compositions of the present invention include two or more purified polypeptides.

As used herein, "treatment" refers to any of (i) the prevention of infection or reinfection, as in a traditional vaccine, (ii) the reduction or elimination of symptomatic disease and or asymptomatic viral shedding, and (iii) the substantial or complete elimination of the pathogen in question. Treatment may be effected prophylactically (prior to infection) or therapeutically (following infection).

By "mammalian subject" is meant any member of the class Mammalia, including, without limitation, humans and non-human primates, such as chimpanzees and other apes and monkey species; farm animals such as cattle, sheep, pigs, goats and horses; domestic mammals such as dogs and cats; and laboratory animals including rodents such as mice, rats and guinea pigs. The term does not denote a particular age. Thus, adult, newborn and fetal mammals are intended to be covered.

II. Modes of Carrying Out the Invention

The present invention is based on the discovery that VP22 is a major CTL target and hence an important antigen in the CTL response to HSV. Thus, the vaccines described herein provide for cellular immunity by the association of VP22 polypeptides with class I MHC molecules. Accordingly, an in vivo cellular immune response to VP22 can be mounted which stimulates the production of CTLs to allow for future recognition of the antigen.

In particular, $CD8^+$, class I-restricted, HSV-specific CTL were cloned from individuals with frequently recurrent herpes to use as tools to identify one or more prominent targets of the cellular response. Because $CD8^+$ CTLs recognize viral antigens after intracellular processing, identification of how many and which viral gene products are recognized by CTL requires reagents and methodologies that deliver identifiable proteins into the cytoplasm in target cells so that they may be processed and presented. As described further below in the examples, several approaches were therefore used to identify the antigens recognized by these clones including: (1) limiting the transcription class of viral gene expression, e.g., immediate early, early, late, etc., with drugs; (2) HSV-1xHSV-2 intertypic recombinant viruses that included discrete segments of the HSV-2 genome within an HSV-1 genomic background; (3) synthetic peptides; and (4) recombinant vaccinia viruses expressing specific HSV genes. Using such techniques, it was found that VP22 was indeed recognized by HSV-specific CD8$^+$ CTL and is therefore useful in vaccine compositions for the treatment and prevention of HSV infection.

Furthermore, the VP22-containing compositions of the present invention can include other HSV polypeptides capable of eliciting cellular and/or humoral immune responses. For example, HSV VP16, a tegument protein, has also been shown to elicit a cellular immune response. Thus, the vaccines of the present invention can include this or other tegument proteins capable of eliciting such responses. Furthermore, HSV glycoproteins, as defined above, such as HSV gB, gD, etc., have been shown to be efficacious in both prophylactic and therapeutic contexts. See, e.g., Burke et al., *Virology* (1991) 181:793–797; Burke et al., *Rev. Infect. Dis.* (1991) 13(Suppl 11):S906–S911; Straus et al., *Lancet* (1994) 343:1460–1463; Ho et al., *J. Virol.* (1989) 63:2951–2958; Stanberry et al., *J. Infect. Dis.* (1988) 157:156–163; and Stanberry et al., (1987) *J. Infect. Dis.* 155:914–920; Stanberry, L. R. "Subunit Viral Vaccines: prophylactic and therapeutic use." In: Aurelian L (ed.) *Herpesviruses, the Immune Systems and Aids.* Kluwer, Boston, pp. 309–341. These glycoproteins elicit a humoral immune response and, when present in the subject compositions, will provide for a vaccine capable of eliciting both cellular and humoral immunity.

The polypeptides for use in the subject vaccines can be produced using a variety of techniques. For example, the HSV polypeptides, such as the desired tegument proteins and/or glycoproteins, can be isolated directly from natural sources using methods well known in the art. Generally, such methods entail isolating the polypeptides of interest from infected sera or from viruses propagated in tissue culture. For example, virions can be purified as described by Spear and Roizman, *J. Virol.* (1972) 9:143–159. Briefly, the method involves careful extraction of cytoplasm to prevent nuclear breakage, separation of enveloped nucleocapsids from soluble proteins and membrane vesicles by rate zonal centrifugation of cytoplasmic extracts through several dextran gradients, treatment with urea to dissociate virus-debris aggregates and separation of virions from naked nucleocapsids and free membranes by isopycnic flotation in discontinuous sucrose gradients. Proteins can be further purified using such methods as column chromatography, electrophoresis, HPLC, immunoadsorbent techniques, affinity chromatography and immunoprecipitation. Any of the various HSV-1 and HSV-2 strains can be used as a source of the desired tegument and glycoproteins.

The HSV tegument polypeptides and glycoproteins can also be generated using recombinant methods, well known in the art. For example methods of recombinantly producing several HSV gB and gD polypeptides are described in, e.g., U.S. Pat. No. 5,171,568; Stanberry et al., *J. Infect. Dis.* (1987) 155:914–920; and Stanberry et al., *J. Gen. Virol.* (1989) 70:3177–3185. Methods for recombinantly producing VP16 polypeptides are described in, e.g., EP Publication No. 541,692 and Triezenberg et al., *Genes and Develop.* (1988) 2:718. Methods for recombinantly producing HSV VP22 are described in, e.g., Leslie et al., *Virology* (1996) 220:60–68 and Elliott and Meredith, *J. Gen. Virol.* (1992) 73:723–726.

These and other HSV tegument polypeptides and glycoproteins can be recombinantly produced as follows. In general, for recombinant production, oligonucleotide probes can be devised based on the known sequences of the HSV genome and used to probe genomic or cDNA libraries for HSV genes coding for the polypeptides useful in the present invention. In this regard, the nucleotide sequence for HSV-1 UL49, the gene encoding VP22, is reported in McGeoch et al., *J. gen. Virol.* (1988) 69:1531–1574 and can be used as a basis for probe design. The genes can then be further isolated using standard techniques and, if desired, PCR approaches or restriction enzymes employed to delete portions of the full-length sequence. For example, in the case of HSV glycoproteins, it may be desirable to delete all or a portion of the transmembrane binding and cytoplasmic domains, as described above, to provide for increased yields of the polypeptides.

Similarly, HSV genes can be isolated directly from cells and tissues containing the same, using known techniques, such as phenol extraction and the sequence further manipulated to produce any desired alterations. See, e.g., Sambrook et al., supra, for a description of techniques used to obtain and isolate DNA. Finally, the genes encoding the HSV polypeptides can be produced synthetically, based on the known sequences. The nucleotide sequence can be designed with the appropriate codons for the particular amino acid sequence desired. In general, one will select preferred codons for the intended host in which the sequence will be expressed. The complete sequence is generally assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J. Biol. Chem.* (1984) 259:6311.

Once coding sequences for the desired HSV polypeptides have been isolated or synthesized, they can be cloned into any suitable vector or replicon for expression in a variety of systems, including insect, mammalian, bacterial, viral and yeast expression systems, all well known in the art. In particular, host cells are transformed with expression vectors which include control sequences operably linked to the desired coding sequence.

The control sequences will be compatible with the particular host cell used. For example, typical promoters for mammalian cell expression include the SV40 early promoter, mouse mammary tumor virus LTR promoter, adenovirus major late promoter (Ad MLP), the cytomegalovirus immediate early promoter, and herpes simplex virus promoter, among others. Other non-viral promoters, such as a promoter derived from the murine metallothionein gene, will also find use in mammalian constructs. Mammalian expression may be either constitutive or regulated (inducible), depending on the promoter. Typically, transcription termination and polyadenylation sequences will also be present, located 3' to the translation stop codon. Examples of transcription terminator/polyadenylation signals include those derived from SV40 and bovine growth hormone (Sambrook et al., supra). Introns, containing splice donor and acceptor sites, may also be designed into the constructs of the present invention.

Enhancer elements can also be used in the mammalian constructs to increase expression levels. Examples include the SV40 early gene enhancer (Dijkema et al., *EMBO J.* (1985) 4:761) and the enhancer/promoters derived from the long terminal repeat (LTR) of the Rous Sarcoma Virus (Gorman et al., *Proc. Natl. Acad. Sci. USA* (1982b) 79:6777) and human cytomegalovirus (Boshart et al., *Cell* (1985) 41:521). A leader sequence can also be present which includes a sequence encoding a signal peptide, to provide for the secretion of the foreign protein in mammalian cells.

Preferably, there are processing sites encoded between the leader fragment and the gene of interest such that the leader sequence can be cleaved either in vivo or in vitro. The adenovirus tripartite leader is an example of a leader sequence that provides for secretion of a foreign protein in mammalian cells.

Once complete, the mammalian expression vectors can be used to transform any of several mammalian cells. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei. Mammalian cell lines available as hosts for expression are also known and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), as well as others.

The constructs of the present invention can also be expressed in yeast. Control sequences for yeast vectors are known in the art and include promoters such as alcohol dehydrogenase (ADH) (EP Publication No. 284,044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EP Publication No. 329,203). The yeast PHO5 gene, encoding acid phosphatase, also provides useful promoter sequences (Myanohara et al., *Proc. Natl. Acad. Sci. USA* (1983) 80:1). In addition, synthetic promoters which do not occur in nature also function as yeast promoters. For example, upstream activating sequences (UAS) of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EP Publication No. 164,556). Furthermore, a yeast promoter can include naturally occurring promoters of non-yeast origin that have the ability to bind yeast RNA polymerase and initiate transcription.

Other control elements which may be included in the yeast expression vectors are terminators (e.g., from GAPDH and from the enolase gene (Holland, *J. Biol. Chem.* (1981) 256:1385), and leader sequences which encode signal sequences for secretion. DNA encoding suitable signal sequences can be derived from genes for secreted yeast proteins, such as the yeast invertase gene (EP Publication No. 012,873; JPO Publication No. 62,096,086) and the α-factor gene (U.S. Pat. Nos. 4,588,684, 4,546,083 and 4,870,008; EP Publication No. 324,274; PCT Publication No. WO 89/02463). Alternatively, leaders of non-yeast origin, such as an interferon leader, also provide for secretion in yeast (EP Publication No. 060,057)

Expression and transformation vectors, either extrachromosomal replicons or integrating vectors, have been developed for transformation into many yeasts. For example, expression vectors have been developed for, inter alia, the following yeasts: *Saccharomyces cerevisiae* (Hinnen et al., *Proc. Natl. Acad. Sci. USA* (1978) 75:1929; Ito et al., *J. Bacteriol.* (1983) 153:163); *Saccharomyces carlsbergeneis; Candida albicans* (Kurtz et al., *Mol. Cell. Biol.* (1986) 6:142); *Candida maltosa* (Kunze et al., *J. Basic Microbiol.* (1985) 25:141); *Hansenula polymorpha* (Gleeson et al., *J. Gen. Microbiol.* (1986) 132:3459; Roggenkamp et al., *Mol. Gen. Genet.* (1986) 202:302); *Kluyveromyces fragilis* (Das et al., *J. Bacteriol.* (1984) 158:1165); *Kluyveromyces lactis* (De Louvencourt et al., *J. Bacteriol.* (1983) 154:737; Van den Berg et al., *Bio/Technology* (1990) 8:135); *Pichia guillerimondii* (Kunze et al., *J. Basic Microbiol.* (1985) 25:141); *Pichia pastoris* (Cregg et al., *Mol. Cell. Biol.* (1985) 5:3376; U.S. Pat. Nos. 4,837,148 and 4,929,555); *Schizosaccharomyces pombe* (Beach and Nurse, Nature (1981) 300:706); and *Yarrowia lipolytica* (Davidow et al., *Curr. Genet.* (1985) 10:380471; Gaillardin et al., *Curr. Genet.* (1985) 10:49).

Methods of introducing exogenous DNA into such yeast hosts are well known in the art, and typically include either the transformation of spheroplasts or of intact yeast cells treated with alkali cations.

Bacterial expression systems can also be used with the present constructs. Control elements for use in bacteria include promoters, optionally containing operator sequences, and ribosome binding sites. Useful promoters include sequences derived from sugar metabolizing enzymes, such as galactose, lactose (lac) and maltose. Additional examples include promoter sequences derived from biosynthetic enzymes such as tryptophan (trp), the b-lactamase (bla) promoter system, bacteriophage lambda PL, and T5. In addition, synthetic promoters, such as the tac promoter (U.S. Pat. No. 4,551,433), which do not occur in nature also function as in bacterial host cells.

The foregoing systems are particularly compatible with *E. coli*. However, numerous other systems for use in bacterial hosts such as Bacillus spp., Streptococcus spp., and Streptomyces spp., among others, are also known. Methods for introducing exogenous DNA into these hosts typically include the use of $CaCl_2$ or other agents, such as divalent cations and DMSO. DNA can also be introduced into bacterial cells by electroporation.

Other systems for expression of the desired polypeptides include insect cells and vectors suitable for use in these cells. The systems most commonly used are derived from the baculovirus *Autographa californica* polyhedrosis virus (AcNPV). Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene into the baculovirus genome); and appropriate insect host cells and growth media.

Promoters for use in the vectors are typically derived from structural genes, abundantly transcribed at late times in a viral infection cycle. Examples include sequences derived from the gene encoding the viral polyhedron protein, Friesen et al., (1986) "The Regulation of Baculovirus Gene Expression" in: *The Molecular Biology of Baculoviruses* (ed. Walter Doerfler); EP Publication Nos. 127,839 and 155,476; and the gene encoding the p10 protein Vlak et al., *J. Gen. Virol.* (1988) 69:765. The plasmid usually also contains the polyhedrin polyadenylation signal (Miller et al., *Ann. Rev. Microbiol.* (1988) 42:177) and a procaryotic ampicillin-resistance (amp) gene and origin of replication for selection and propagation in *E. coli*. DNA encoding suitable signal sequences can also be included and is generally derived from genes for secreted insect or baculovirus proteins, such as the baculovirus polyhedrin gene (Carbonell et al., *Gene* (1988) 73:409), as well as mammalian signal sequences such as those derived from genes encoding human α-interferon, Maeda et al., *Nature* (1985) 315:592; human gastrin-releasing peptide, Lebacq-Verheyden et al., *Molec. Cell. Biol.* (1988) 8:3129; human IL-2, Smith et al., *Proc. Natl. Acad. Sci. USA* (1985) 82:8404; mouse IL-3, (Miyajima et al., *Gene* (1987) 58:273; and human glucocerebrosidase, Martin et al., *DNA* (1988) 7:99.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 bps downstream from the ATT; see Luckow and Summers, *Virology* (1989) 17:31).

The desired DNA sequence is inserted into the transfer vector, using known techniques (see, Summers and Smith, supra; Smith et al., *Mol. Cell. Biol.* (1983) 3:2156; and Luckow and Summers (1989) and an insect cell host is cotransformed with the heterologous DNA of the transfer vector and the genomic DNA of wild type baculovirus—usually by cotransfection. The vector and viral genome are allowed to recombine. The packaged recombinant virus is expressed and recombinant plaques are identified and purified. Materials and methods for baculovirus/insect cell expression systems are commercially available in kit form from, for example, Invitrogen, San Diego Calif. ("MAXBAG™" kit). These techniques are generally known to those skilled in the art and fully described in Summers and Smith, *Texas Agricultural Experiment Station Bulletin No.* 1555 (1987).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda,* and *Trichoplusia ni.*

It is often desirable that the polypeptides prepared using the above systems be fusion polypeptides. As with non-fusion proteins, these proteins may be expressed intracellularly or may be secreted from the cell into the growth medium.

Furthermore, plasmids can be constructed which include a chimeric gene sequence, encoding e.g., a VP22 polypeptide as well as other HSV polypeptides of interest such as VP16, HSV gB, HSV gD, etc., polypeptides. Additionally, genes coding for immune modulating agents which can enhance antigen presentation, attract lymphocytes to the antigen or which promote expansion of the population of lymphocytes which respond to the antigen, can also be present. Such agents include cytokines, lymphokines, and chemokines, including but not limited to IL-2, modified IL-2 (cys125→ser125), GM-CSF, IL-12, γ-interferon, IL-10, MIP1α, MIP1β and RANTES.

If present, the additional gene sequences can either precede or follow the gene encoding the VP22 polypeptide in a dicistronic gene configuration. Additional control elements can be situated between the various genes for efficient translation of RNA from the distal coding region. Alternatively, a chimeric transcription unit having a single open reading frame encoding VP22 and additional HSV polypeptides or other immune modulating agents, can also be constructed. Either a fusion can be made to allow for the synthesis of a chimeric protein or alternatively, protein processing signals can be engineered to provide cleavage by a protease such as a signal peptidase, thus allowing liberation of the two or more proteins derived from translation of the template RNA. The processing protease may also be expressed in this system either independently or as part of a chimera with the antigen and/or cytokine coding region(s). The protease itself can be both a processing enzyme and a vaccine antigen.

Once expressed, the polypeptides can be purified from the above-described host cells using any of several techniques known in the art. If the expression system secretes the protein into growth media, the protein can be purified directly from the media. If the protein is not secreted, it is isolated from cell lysates. The protein can then be further purified using techniques known in the art, such as column chromatography, HPLC, immunoadsorbent techniques, affinity chromatography and immunoprecipitation. Activity of the purified proteins can be determined using standard assays, based on specific properties of the various native proteins.

The HSV polypeptides may also be produced by chemical synthesis such as by solid phase or solution peptide synthesis, using methods known to those skilled in the art. Chemical synthesis of peptides may be preferable if the polypeptide in question is relatively small. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology,* editors E. Gross and J. Meienhofer, Vol. 2, Academic Press, New York, (1980), pp. 3–254, for solid phase peptide synthesis techniques; and M. Bodansky, *Principles of Peptide Synthesis,* Springer-Verlag, Berlin (1984) and E. Gross and J. Meienhofer, Eds., *The Peptides: Analysis, Synthesis, Biology,* supra, Vol. 1, for classical solution synthesis.

Once obtained, the HSV polypeptides are formulated into vaccine compositions to treat or prevent HSV infection in a mammalian subject. Thus, the compositions may either be prophylactic (to prevent infection) or therapeutic (to treat disease after infection). The vaccine compositions will comprise an "effective amount" of the VP22 polypeptide, and any additional HSV polypeptides such that a cellular immune response, and if other HSV polypeptides are present, a humoral immune response, can be generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular HSV polypeptide in question and its mode of administration, among other factors. An appropriate effective amount can be readily determined by one of skill in the art. Thus, an "effective amount" will fall in a relatively broad range that can be determined through routine trials. For example, for purposes of the present invention, an effective dose will be from about 5 µg to about 250 µg antigen per dose.

The vaccine compositions will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes, described further below), and inactive virus particles. Such carriers are well known to those of ordinary skill in the art. Particulate carriers will find use with the present invention and include those derived from polymethyl methacrylate polymers, as well as microparticles derived from poly(lactides) and poly(lactide-co-glycolides), known as PLG. See, e.g., Jeffery et al., *Pharm. Res.* (1993) 10:362–368; and McGee et al., *J. Microencap.* (1996). Additionally, these carriers may function as immunostimulating agents ("adjuvants"). Furthermore, the antigen may be conjugated to a bacterial toxoid, such as toxoid from diphtheria, tetanus, cholera, *E. coli*, etc.

Adjuvants may also be used to enhance the effectiveness of the vaccine compositions. Adjuvants can be either added directly to the vaccine compositions or can be administered concurrently with, or shortly before or after, administration of the vaccine composition. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 ™(International Publication No. WO 90/14837), containing 5% Squalene, 0.5% TWEEN™ 80, and 0.5% SPAN™ 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% TWEEN™ 80, 5% pluronic-blocked polymer L121, and thr-MDP (see below) either microfluidized into a submicron emulsion or vortexed to generate a larger particle size emulsion, and (c) RIBI™ ™ adjuvant system (RAS), (Ribi Immunochem, Hamilton, Mont.) containing 2% Squalene, 0.2% TWEEN™ 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as STIMULEN™ (Cambridge Bioscience, Worcester, Mass.) may be used or particle generated therefrom such as ISCOMs (immunostimulating complexes) and ISCOMATRIX;™(4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition. Alum and MF59 are preferred.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

Once formulated, the compositions of the invention can be administered parenterally, e.g., by injection. The compositions can be injected either subcutaneously, intraperitoneally, intravenously or intramuscularly. Other modes of administration include oral and pulmonary administration, suppositories, and transdermal applications. Dosage treatment may be a single dose schedule or a multiple dose schedule. A multiple dose schedule is one in which a primary course of vaccination may be with 1–10 separate doses, followed by other doses given at subsequent time intervals, chosen to maintain and/or reinforce the immune response, for example at 1–4 months for a second dose, and if needed, a subsequent dose(s) after several months. The dosage regimen will also, at least in part, be determined by the need of the subject and be dependent on the judgment of the practitioner. Furthermore, if prevention of disease is desired, the vaccines are generally administered prior to primary infection with HSV. If treatment is desired, e.g., the reduction of symptoms or recurrences, the vaccines are generally administered subsequent to primary infection with HSV.

An alternative route of administration involves nucleic acid immunization. Thus, nucleotide sequences encoding the subject proteins (and, if appropriate, accompanying regulatory elements) can be used for nucleic acid immunization using standard gene delivery protocols. Methods for gene delivery are known in the art. See, e.g., U.S. Pat. No. 5,399,346. Genes can be delivered either directly to the mammalian subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980–990; Miller, A. D., *Human Gene Therapy* (1990) 1:5–14; Scarpa et al., *Virology* (1991) 180:849–852; Burns et al., *Proc. Natl. Acad. Sci. USA* (1993) 90:8033–8037; and Boris-Lawrie and Temin, *Cur. Opin. Genet. Develop.* (1993) 3:102–109. A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267–274; Bett et al., *J. Virol.* (1993) 67:5911–5921; Mittereder et al., *Human Gene Therapy* (1994) 5:717–729; Seth et al., *J. Virol.* (1994) 68:933–940; Barr et al., *Gene Therapy* (1994) 1:51–58; Berkner, K. L. *BioTechniques* (1988) 6:616–629; and Rich et al., *Human Gene Therapy* (1993) 4:461–476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al., *Molec. Cell. Biol.* (1988) 8:3988–3996; Vincent et al., *Vaccines* 90 (1990) (Cold Spring Harbor Laboratory Press); Carter, B. J. *Current Opinion in Biotechnology* (1992) 3:533–539; Muzyczka, N. *Current Topics in Microbiol. and Immunol.* (1992) 158:97–129; Kotin, R. M. *Human Gene Therapy* (1994) 5:793–801; Shelling and Smith, *Gene Therapy* (1994)

1:165–169; and Zhou et al., *J. Exp. Med.* (1994) 179:1867–1875.

Additional viral vectors which will find use for delivering the nucleic acid molecules encoding the antigens of interest include those derived from the pox family of viruses, including vaccinia virus and avian poxvirus. By way of example, vaccinia virus recombinants expressing the genes can be constructed as follows. The DNA encoding the particular polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the protein into the viral genome. The resulting TK$^{31}$ recombinant can be selected by culturing the cells in the presence of 5-bromodeoxyuridine and picking viral plaques resistant thereto.

A vaccinia based infection/transfection system can be conveniently used to provide for inducible, transient expression of the gene of interest in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743–6747; Fuerst et al., *Proc. Natl. Acad. Sci. USA* (1986) 83:8122–8126.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.* (1993) 268:6866–6869 and Wagner et al., *Proc. Natl. Acad. Sci. USA* (1992) 89:6099–6103, can also be used for gene delivery.

Members of the Alphavirus genus, such as but not limited to vectors derived from the Sindbis and Semliki Forest viruses, will also find use as viral vectors for delivering the VP22 gene. For a description of Sinbus-virus derived vectors useful for the practice of the instant methods, see, Dubensky et al., *J. Virol.* (1996) 70:508–519; and International Publication Nos. WO 95/07995 and WO 96/17072.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, *J. Mol. Biol.* (1986) 189:113–130; Deng and Wolff, *Gene* (1994) 143:245–249; Gao et al., *Biochem. Biophys. Res. Commun.* (1994) 200:1201–1206; Gao and Huang, *Nuc. Acids Res.* (1993) 21:2867–2872; Chen et al., *Nuc. Acids Res.* (1994) 22:2114–2120; and U.S. Pat. No. 5,135,855.

Vectors encoding the gene of interest can also be packaged in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1–17; Straubinger et al., in *Methods of Enzymology* (1983), Vol. 101, pp. 512–527.

Liposomal preparations for use in the instant invention include cationic (positively charged), anionic (negatively charged) and neutral preparations, with cationic liposomes particularly preferred. Cationic liposomes have been shown to mediate intracellular delivery of plasmid DNA (Felgner et al., *Proc. Natl. Acad. Sci. USA* (1987) 84:7413–7416); mRNA (Malone et al., *Proc. Natl. Acad. Sci. USA* (1989) 86:6077–6081); and purified transcription factors (Debs et al., *J. Biol. Chem.* (1990) 265:10189–10192), in functional form.

Cationic liposomes are readily available. For example, N[1–2,3-dioleyloxy)propyl]-N,N,N-triethyl-ammonium (DOTMA) liposomes are available under the trademark LIPOFECTIN™, from GIBCO BRL, Grand Island, N.Y. (See, also, Felgner et al., *Proc. Natl. Acad. Sci. USA* (1987) 84:7413–7416). Other commercially available liposomes include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194–4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al. in METHODS OF IMMUNOLOGY (1983), Vol. 101, pp. 512–527; Szoka et al., *Proc. Natl. Acad. Sci. USA* (1978) 75:4194–4198; Papahadjopoulos et al., *Biochim. Biophys. Acta* (1975) 394:483; Wilson et al. *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA can also be delivered in cochleate lipid compositions similar to those described by Papahadjopoulos et al., *Biochem. Biophys. Acta.* (1975) 394:483–491. See, also, U.S. Pat. Nos. 4,663,161 and 4,871,488.

The VP22 gene may also be encapsulated, adsorbed to, or associated with, particulate carriers. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly (lactide-co-glycolides), known as PLG. See, e.g., Jeffery et al., *Pharm. Res.* (1993) 10:362–368; and McGee et al., *J. Microencap.* (1996).

Furthermore, other particulate systems and polymers can be used for the in vivo or ex vivo delivery of the VP22 gene. For example, polymers such as polylysine, polyarginine, polyornithine, spermine, spermidine, as well as conjugates of these molecules, are useful for transferring the VP22 gene. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., *Advanced Drug Delivery Reviews* (1990) 5:163–187, for a review of delivery systems useful for gene transfer.

Additionally, biolistic delivery systems employing particulate carriers such as gold and tungsten, are especially useful for delivering genes of interest. The particles are coated with the gene to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

The recombinant vectors (whether or not encapsulated in liposomes), are formulated into compositions for delivery to the mammalian subject as described above. The compositions will comprise an "effective amount" of the gene of interest such that an amount of the antigen can be produced so that an immune response is generated in the individual to which it is administered, as described above. Also as explained above, the exact amount necessary will vary depending on several factors and can be readily determined by one of skill in the art. For purposes of the present invention, an effective dose will be from about 1 μg to about 100 mg, more preferably from about 10 μg to about 1 mg, of the DNA constructs. Dosage regimens are as described above.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Materials and Methods

Viruses

All HSV virus stocks with the exception of hr259 were propagated on Vero cells. Virus stocks were prepared on sub-confluent monolayers by infection at low multiplicity and the virus was released from the concentrated cells by sonication. The ICP4$^-$ mutant hr259 was grown on E5 cells, a Vero line stably transfected with and expressing HSV-1 ICP4 (DeLuca et al., *J. Virol.* (1985) 56:558–570; Smith and Schaffer, *J. Virol.* (1987) 61:1092–1097) in the same manner. The HSV-1xHSV-2 recombinant viruses were obtained from Bernard Roizman. They were constructed by cotransfection of HSV-1 (strain F) DNA and restriction fragments from HSV-2 (strain G) into rabbit skin cells and isolating recombinants by enhanced surface immunoassay as described (Purves et al., *J. Virol.* (1994) 65:5757–5764; Ackermann et al., *Virology* (1994) 150:207–220.

Recombinant vaccinia viruses were constructed by insertion of the HSV-2 open reading frames (ORFs) UL48 (encoding VP16), UL49 (encoding VP22), UL46 or UL47 into the vaccinia shuttle vector pSC11.1 (Chakrabarti et al., "Vaccinia virus expression vector: coexpression of beta-galactosidase provides visual screening of recombinant virus plaques," *Mol. Cell Biol.* 5(12):3403–3409 (1985)). This is a pUC8 plasmid containing a vaccinia tk gene split by an *E. coli* lacZ gene driven by the vaccinia late p11 promoter with an adjacent polylinker site driven by the early/late p7.5 promoter. The HSV ORF-containing fragment was inserted into the polylinker and proper orientation of the inserts were verified by diagnostic restriction digests which corroborated both the presence and orientation of the insert. The construction of the vac/VP16 recombinant is described in EP Publication No. 541,692. Both full-length VP16 vaccinia recombinants, termed "vac/VP16$_{FL}$" herein, and truncated VP16 recombinants, including a gene encoding amino acids 1–416, termed "vac/VP16t" herein, were made.

Cloning and Expression of UL49

The HSV-2 UL49 gene was subcloned from the plasmid, pH2G-512 containing the Eco RI fragment L of HSV-2 provided by Phil Pellet, by PCR using primers complementary to the 5'- and 3'- ends of the UL49 ORF and each containing a BglII restriction site. A glu epitope tag was also encoded by the 3' primer. This tag facilitates the identification, quantification and purification of any protein bearing it by the use of a corresponding monoclonal anti body that specifically recognizes the glu epitope. The primer pair used for the PCR reaction consisted of a 27 nucleotide oligomer (GPUL49 5') and 54 nucleotide oligomer (GPUL49 3') with the following sequences:

```
GPUL49 5':
5'GGTACCAGATCTATGACCTCTCGCCGC3'          (SEQ ID NO:4)

GPUL49 3':
5'CTCTGCAGATCTCTATTCCATTGGCATGTATTCCT   (SEQ ID NO:5)
CGAGGGGCGGCGGGGAGCG
```

The UL49 ORF was amplified in standard buffer containing 5% formamide, 0.2 µg/ml of the pH2G-512 plasmid, primers and vent Taq using the following conditions: 5 min at 97° C.; 15 cycles×54 sec at 96° C.; 54 sec at 67° C.; 54 sec at 72° C.; and 10 min at 72° C.

The expected 900 bp band was resolved in preparative agarose gels, extracted, ethanol precipitated, and cut with BglII. After a second gel purification, the fragment was ligated into the baculovirus shuttle vector plasmid pAC13 which had previously been cut with BglII and treated with alkaline phosphatase (see FIG. 2). The ligated DNA was used to transform E. coli. Twenty colonies were randomly selected and their plasmid DNA was isolated and tested by PCR using the 5'- and 3'-UL49 primers. Four clones contained plasmids that yielded the expected PCR product. The presence and the integrity of the UL49 gene was verified by restriction digest with BglII, KpnI+StuI or PstI. Plasmid DNA from one of the clones with the expected pattern was sequenced to verify the insert. The plasmid was termed pAcUL49. FIGS. 1A–1B (SEQ ID NOS:1–2) show the sequence of the UL49 ORF from pAcUL49 and the predicted amino acid sequence of HSV-2 VP22. One conservative base change (C->T leu->leu) was observed at position 70.

Plasmid pAcUL49 was used to transfect baculovirus-infected insect cells. Five plaque purified isolates were screened for UL49 expression using the anti-glu monoclonal antibody in Western blots. Four of the five expressed a 40 kD protein that reacted with the glu antibody. Although the predicted molecular mass of tagged UL49 protein is 32.7 kD, its mobility in SDS-PAGE may be aberrant due to its highly charged nature (10.75 mole %– and 17.6 mole %+, pI=10.4).

Figure 3:
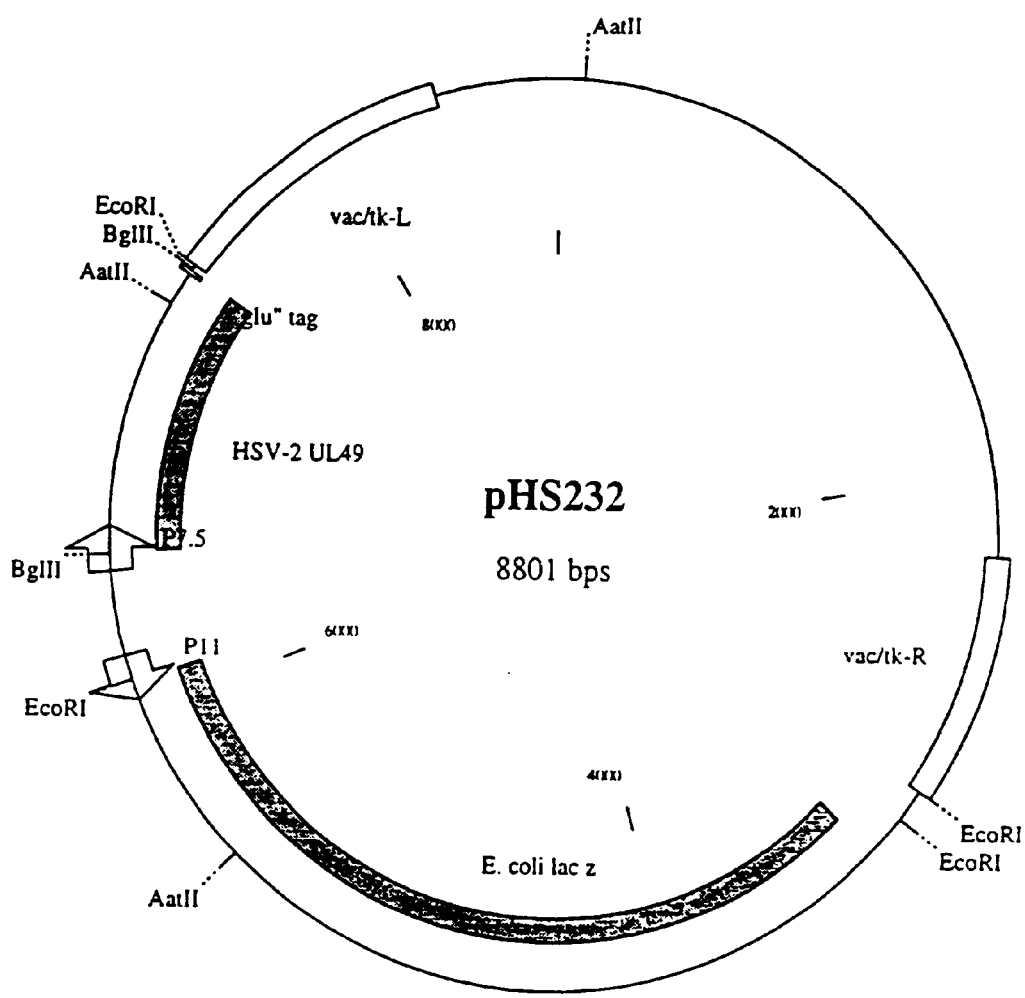
FIG. 3 shows the vaccinia shuttle vector, pHS232, which includes UL49, encoding HSV-2 VP22.

A vaccinia shuttle vector was constructed by gel purifying a 927 bp BglII fragment from pAcUL49, and ligating the fragment with BglII-cut, alkaline phosphatase-treated plasmid pSC11.1. The resulting vector was used to transfect E. coli HB101. Clones were screened for plasmids containing the UL49 insert by restriction digests with AatII. One clone with the proper pattern was designated as pHS232 (FIG. 3) was used for transfection.

To clone the HSV-2 genes UL46 and UL47, the plasmid pHS2G-512 which contained the Eco RI fragment L of HSV-2 EcoL, was sequenced. The locations of the UL46 and UL47 ORFs were identified by their similarity to the corresponding HSV-1 homologue genes (McKnight et al., J. Virol. (1987) 61:992–1001). The ORFs were isolated by PCR using primers that paired with the 5' and 3' regions of the genes that also contained BglII sites and the "glu" tag on the 3'-primer. These genes were then cloned into the plasmid pAc13.

Recombinant plasmids containing UL46 and UL47 in pAc13 were detected in transformed E. coli. The genes were then incorporated into baculoviruses by the same series of steps described above for UL49. The UL46 and UL47 genes were excised from the respective pAc13 plasmid derivatives by BglII digestion and ligated into the vaccinia virus shuttle vector pSC11.1.

Vaccinia recombinant viruses expressing the UL46, 47 or 49 genes were created by infection-transfection of BSC-40 cells essentially as described by Mackett et al. (1987) The construction and characterization of vaccinia virus recombinants expressing foreign genes. In DNA Cloning (IRL Press), pp. 191–211. Sub-confluent monolayers were infected with wild-type vaccinia virus (strain WR) with a multiplicity of infection (m.o.i.)=0.05 for 1 hr prior to the addition of DNA. Transfection was performed by combination of 10 µg of plasmid DNA in 50 µl of water with 30 µl of LIPOFECTIN™ in 20 µl of water in polystyrene tubes for 15 min at room temperature. After 15 min, the transfection mixture was added to 0.5 ml Dulbecco's Minimal Eagle's (DME) medium and in turn placed on the washed, vacWR-infected monolayers. The monolayers were treated with the concentrated DNA:LIPOFECTIN™ mixture for 30 min before the addition of 5 ml $DME_{F10}$ (DME containing 10% fetal bovine serum) After 2 hrs, the medium was removed, the monolayers washed twice with $DME_{F10}$, and the media replaced and cultures incubated for three days.

The cultures were then harvested and either immediately frozen for future use or sonicated three times (horn sonicator at setting 7, 3×30 sec intervals on ice) before being diluted for plaque purification. Serial dilutions of the recombinant viruses (tk⁻, β-gal⁺) were selected on TK-143b cells in the presence of 12.5 µg/ml of BuDR (Bromodeoxy Uridine) and 1% low gelling temperature (LGT) agarose. Two days after the plaque assay was set up, recombinant plaques were detected using X-gal (15 µl of 2% stock per well of the assay plates) in 1 ml of a 1% LGT agarose: $DME_{F10}$ overlay. Plaques that stained blue were selected by aspiration of the agarose plug and underlying plaque with a disposable polyethylene transfer pipette into 0.5 ml DME. The selected plaques were subjected to two additional rounds of amplification on BSC-40 cells and selection on TK-143b cells.

Expression of the HSV-2 genes was confirmed for all three recombinants (UL46, 47 and 49) using Western blots of extracts of infected cells probed with anti-glu monoclonal antibody and with a commercial anti-HSV-2 polyclonal rabbit antibody. Once expression was confirmed, virus stocks were grown on BSC-40 cells and purified on sucrose cushions.

Preparation of HSV-specific CD8⁺ CTL Clones

HSV-specific CD8⁺ CTL from three donors with recurrent genital herpes were cloned after restimulation with virus-infected PBMC as previously described (Tigges et al., J. Virol. (1992) 66:1622–1634). Before being used in $^{51}$Cr release assays, the T cells were recovered from cryopreservation and restimulated either with PHA (1 µg/ml) or with 10 µg of anti-CD3 monoclonal antibody (OKT3) plus 10 µg of anti-CD8 monoclonal antibody (leu2) bound to protein A-Sepharose beads. The restimulation cultures contained 2×10⁵ T-cells, 2×10⁵ B-LCL (γ irradiated with 7,500 rad), 2×10⁶ freshly prepared, allogeneic PBMC (γ irradiated with 3000 rad) in 2 ml of RPMI-CM. (RPMI-CM is RPMI 1640 supplemented with 2 mM L-glutamine, 10 mM HEPES, pH 7.2, 1% MEM non-essential amino acids, 10 mM MEM-vitamins, 1 mM Na pyruvate, 20 µg/ml asparagine, 2×10⁻⁵ M 2-mercaptoethanol, 50 µg/ml gentamycin, and 10% heat-inactivated, pooled human serum.) IL-2 (32 U/ml) from PHA-stimulated human PBMC was added to cultures stimulated with monoclonal antibodies. For PHA-stimulated cultures, the medium was replaced with 2 ml of RPMI-CM containing IL-2 after 48 hours.

$^{51}$Cr Release Assays

Autologous target B-LCL were prepared by infection with the appropriate virus (HSV or recombinant vaccinia virus) and incubated for 3 to 18 hr. The cells were then collected and concentrated into 0.2 ml of medium containing $^{51}$Cr. After a 90 min incubation, the unincorporated $^{51}$Cr was washed away and $10^4$ cells were added to triplicate wells of a 96 well plate containing the CTL. The CTL had previously been collected from the restimulation culture, washed and $10^5$ cells were dispensed into V-bottom 96-well plates. Portions of the CTL were also diluted in two four-fold steps to achieve effector:target ratios of 10:1, 2.5:1 and 0.625:1. After adding the target B-LCL, the plates were briefly centrifuged at low speed and then incubated at 37° C. for four hrs. Spontaneous release of $^{51}$Cr was determined from wells containing only target cells in medium. Total release was determined by adding 1% NP-40 to wells containing target cells. After the incubation period, 100 µl of the supernatant was removed for counting and calculation of specific release.

$$\frac{\% \text{ specific}}{\text{release}} = \frac{(\text{avg. cpm released} - \text{avg. spontaneous release}) \times 100}{(\text{avg. total release} - \text{avg. spontaneous release})}$$

Limiting Dilution Analysis Assays (LDA)

Quantitative determination of CTLs were made using a limiting dilution assay based on the single hit Poisson model as described by Taswell, *J. Immunol.* (1981) 126:1614–1619 and MacDonald et al., *Immunol. Rev.* (1980) 51:93–123. To set up the assay, $3\times10^7$ PBMC from selected individuals were recovered from cryopreservation and $10^6$ cells were reserved for use as stimulator cells. These PBMC were placed in 0.5 ml of serum-free RPMI in a polyethylene tube and infected with an m.o.i.=2, using an HSV-2 virus strain (HG52X163X12), designated as X12, that lacks the ICP47 gene, which encodes an inhibitor of the TAP peptide transporter (York et al., *Nature* (1995) 375(6530):411–415; and Johnson et al., *Cell* (1994) 77:525–535. HSV-2X12 also contains a frame-shift mutation in the vhs gene (Everett and Fenwick, *J. Gen. Virol.* (1990) 71:1387–1390). The effect of these two mutations is to prolong the expression of class I MHC in HSV-infected cells and thus improve the ability of infected cells to serve as antigen presenting cells (APC). After a 1 hr absorption, $\text{RPMI}_{F10}$ was added and the cells were cultured at 37° C. in a 7% $CO_2$ atmosphere overnight.

The remaining cells were then treated with a mouse anti-human CD16 monoclonal antibody to remove Natural Killer cells. After incubation with rotation at 4° C. for 30 min, the CD16$^+$ cells were removed using an anti-mouse Ig conjugated to magnetic beads and discarded. The CD16 depleted cells were next treated with anti-CD8 monoclonal antibody conjugated to magnetic beads with rotation at 4° C. for 30 min. The bound CD8$^+$ cells were then removed with a magnet, washed and put into culture overnight in AIM-V™ medium containing 2% pooled human AB serum and 32 U/ml of IL-2. The unbound cells were irradiated with 3000 R of γ radiation then dispensed into two U-bottom 96-well microtiter plates in 100 µl per well.

The next day, the infected stimulator cells were irradiated with 7500 R of γ radiation, concentrated, and added to 96 well U-bottom plates. The CD8$^+$ cells were freed of the magnetic beads by treatment with DETACH-A-BEAD™ (Dynal) for 1 hr and the beads were removed with a magnet. The number of released CD8$^+$ T cells were determined and graded numbers of cells starting with 30,000 to 50,000 cells/well were added to the U-bottom plates in a seven-step dilution series of 24 replicates each. The dilution steps were adjusted so that the numbers were evenly distributed between the starting number (e.g. 50,000 cells/well) and 500–1,000 cells/well at the $7^{th}$ step. An additional 24 wells received no CD8$^+$ cells and served as controls in the assay. The plates were incubated for 13 days in AIM-V™ medium containing 2% pooled human AB serum and 32 U/ml of IL-2 at 37° C. in 7% $CO_2$ with medium changes every 4 days.

Target cells, which consisted of autologous B-LCL infected with HSV-2 or recombinant vaccinia viruses expressing the genes of interest, were infected the day before the assay, loaded with $^{51}$Cr as described above, and dispensed into V-bottom assay plates. To prepare the assay plates on the day of assay, the two restimulation plates were split into 4 replicates. This was accomplished by first adding 50 µl of medium to each well of the restimulation plates, then resuspending the contents by titration with a 12 channel multi-pipettor and dispensing 50 µl of the resuspend cells to four V-bottom assay plates. An additional 50 µl of medium was added to all but the last column of the second plate which was aspirated and replaced with 100 µl of 1% NP-40. The $^{51}$Cr loaded target cells (5000) were added in 100 µl of medium, the plates were centrifuged for 1 min at 900 rpm in plate holders, and incubated at 37° C. for 4 hr. After incubation, the plates were centrifuged briefly again and 50 µl was transferred to 96-well LUMAPLATES™ (Packard Instruments). After drying, the plates were counted in a Wallac MicroBeta counter and the data analyzed. For most assays the cutoff between positive and negative wells was determined as being above 10–15% specific release rather than 3 SD above the mean of spontaneous release.

Results

HSV-2 VP22 (encoded by UL49) was identified as a major target of the human HSV-specific CD8$^+$ CTL response based on the number of CTL clones that recognized VP22 from a library of 22 CTL clones established from humans with recurrent genital herpes. These clones were isolated as described by Tigges et al. Subsequently, additional CTL were isolated from this individual as well as from two other individuals, subjects 3 and 4. In total, 22 clones were isolated and propagated for a sufficient amount of time to partially or completely characterize them.

To help identify the exact HSV protein recognized by the CTL, the CTL clones were characterized with respect to HSV-1 or HSV-2 type-specificity, the timing of epitope expression following infection of target cells and the location of the target gene on the viral genome.

The HSV-type specificity of the CTL clones was determined by their ability to recognize HSV-1 or HSV-2-infected cells or both. Determining the timing of presentation of the HSV protein following infection helps to identify the target protein since HSV genes are expressed in a temporal cascade of immediate early, early and late genes following infection. By using selective drugs or viral mutants, it is possible to block all viral gene expression following infection or to limit gene expression to genes of the immediate early, or immediate early plus early classes. The use of this strategy is described in Tigges et al. (1992) op. cite. Finally the rough location of the genes encoding the HSV target proteins can be determined for the HSV-type specific CTL clones using HSV type 1/type 2 intertypic recombinant viruses. Fine mapping is accomplished by using target cells infected with recombinant vaccinia viruses expressing specific HSV genes.

Of the 22 clones, 13 recognized target cells infected with HSV-2 and the rest recognized cells infected with either HSV-1 or HSV-2.

Among these clones, one (1-1H6) recognized gD2 since it lysed target cells infected with HSV or recombinant Vaccinia virus expressing gD2 (vac/gD2). A second recognized gB2 since it lysed target cells infected with vac/gB2 (3-8G1) (Table 1). None of the other clones were specific for either of these two glycoproteins.

The observation that proteins that contained within the HSV virus particle represent the predominate targets of the CTL response was determined by completely blocking de novo gene expression in HSV-infected target cells with the transcriptional inhibitor DRB. In these cells, in which no new proteins are being synthesized, the only virus proteins that can be processed and presented as peptides bound to MHC class I molecules to $CD8^+$ CTL are those virus proteins that were introduced into the cell as a result the fusion of the virus and cell membranes and the entry of the virus particle into the cytoplasm. Table 2 shows the results of an experiment in which 9 $CD8^+$ CTL clones are tested for this ability to recognize target cells treated with DRB prior to HSV infection. All 9 clone lysed cells infected with HSV-2 for 18 hours in the absence of drug and of the 8 clones tested also readily lysed cells infected for 3 hrs in the absence of drug with values of specific release exceeding 20%. All 7 of these CTL clones also lysed cells infected for 3 hr in the presence of DRB, a result that implicates virion proteins as the targets of CTL recognition. Since it is possible that DRB treatment alters antigen processing and presentation in some undefined way, we used a second approach to limit de novo virus gene expression in the infected cell. The HSV-2 strain hr259 has a mutation that abrogates expression of the essential immediate early gene ICP4. When this virus infects a noncomplementing cell line, the only HSV genes expressed are the additional four immediate early genes, ICP0, ICP22, ICP27 and ICP47. In the absence of the essential transcriptional transactivator ICP4 no early or late HSV genes are expressed and infection is aborted. As shown in Table 2 when the HSV-specific CTL clones were cultured with target cells infected for 3 hr with HSV-2 hr259, 8 of the 9 CTL clones ably lysed the cells with specific releases exceeding 20%. In these target cells only the virion proteins and the remaining 4 immediate early proteins could be the targets of sensitization. Thus the results of experiments that limit virus gene expression by drug inhibition or virus mutation are concordant.

As shown in Table 2, one of the nine HS-specific CTL clones, 3-8G1, recognized cells infected for 18 hr but poorly lysed cells infected for only 3 hr and failed to lyse cells infected for 3 hr in the presence of DRB or infected for 3 hr with the ICP4 minus mutant strain hr259. As was shown above, this CTL clone recognizes the glycoprotein gB since CTL clone 3-8G1 lyses recombinant vaccinia virus VacgB infected cells. These results imply that the virus glycoproteins are left on the surface of the virus-infected cell when the two membranes fuse. Thus they do not enter the cytoplasm of the infected cell to become substrates for the processing machinery, the proteosome and TAP peptide transporters, that provides peptides that bind to the MHC class I molecules. All have previously shown a similar result for the gD2 specific CTL clone, 1-1H6. (Tigges et al. 1992.) Of all of the remaining CTL clones, only the 1-2E7 clone exhibited any sensitivity to blocks to viral gene expression (see Table 5 in Tigges et al. 1992).

The HSV virion is a complex assembly of proteins and viral DNA. The DNA is surrounded by a dedeca icosahedral capsid of viral proteins. The capsid is surrounded by an amorphous mixture of viral proteins called the tegument which in turn, is encased by the viral membrane containing embedded viral glycoproteins.

Eliminating the glycoproteins as predominate CTL targets left 25–30 additional proteins in the tegument and capsid that are part of the virion. The genes specifying the proteins are scattered throughout the genome (Roizman and Sears, (1993) Herpes simplex viruses and their replication. In *The Human Herpesviruses*. B. Roizman, R. J. Whitley, and C. Lopez, eds. (New York: Raven Press Ltd.), pp. 11–68). The first strategy was to localize as many of the genes encoding the target proteins as possible. This was done for the targets of 12/13 clones that were HSV-2 specific, using six intertypic recombinant viruses that contained nested segments of HSV-2 DNA inserted into a HSV-1 (strain F) genetic background shown in Table 3. The six recombinant viruses spanned three regions of the HSV-2 genome in a nested fashion. The RH 1G7 virus included map units 0.3–0.45 while the nested recombinants RH 1G8 and RH 1G44 included subregions 0.385–0.405 and 0.37 and 0.405 respectively. Similarly, the RS 1G25 virus included HSV-2 DNA from map units 0.59–0.72 and the nested virus included the subregion 0.68–0.72. Finally, recombinant R 7015 included the entire HSV-2 unique short (US) region, the short terminal repeat and internal repeat sequences as well as part of the long internal repeat. These three sets of clones include open reading frames that encode gB2, VP16 and gD2. The one remaining clone had lost antigen-specific lytic activity and so could not be characterized further.

Figure 4:
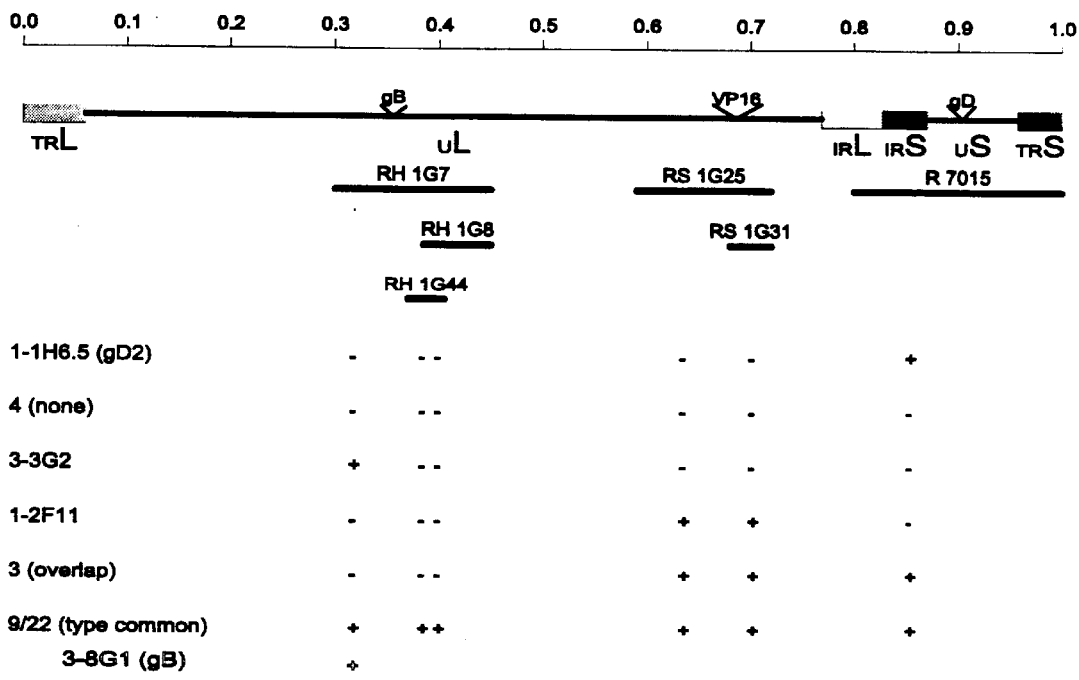
FIG. 4 shows localization of antigens recognized by CD8+, HSV-specific CTL clones using HSV-2xHSV-1 intertypic recombinants, as described in the examples.

Table 3 lists the results of the mapping studies for 2 type common CTL clones, 1-3B3 and 3-8G1, and for 12 of the 13 type-specific clones. FIG. 4 displays the mapping results with respect to the HSV genome and selected marker genes (gB, gD and VP16). As expected, the 1-1H6 gD-2 specific clone mapped to the $U_s$ segment contained in with the HSV-2XHSV-1 intertypic recombinant virus R7015. The two type-common clones, 1-3B3 and 3-8G1, recognized all targets because the epitopes are identical between type 1 and type 2 viruses. Of the remaining clones, one (3-3G2) mapped to the region between map units 0.3–0.385 and four mapped to a region between map units 0.68–0.72. However, three of these clones also recognized R7015-infected targets, suggesting that the genomes of these recombinant viruses are not as simple as mapped. The remaining 7 clones were not mapped, indicating that the genes that supply epitopes for these clones lie outside the regions represented in the panel.

The four clones that mapped to the 0.68–0.72 segment were further analyzed using an intertypic recombinant virus (RP-2) that contained the UL48 (VP16) ORF from HSV-2 recombined into a ΔVP16 HSV-1 (strain KOS) mutant (Weinheimer et al., *J. Virol.* (1992) 66:258–269; Koelle et al., *J. Virol.* (1994) 68:2803–2810). Two additional, type-common clones were also included in this experiment as controls. The results shown in Table 4 demonstrate that the three clones that shared the double phenotype (i.e. mapping to both the 0.68–0.72 map units and $U_s$ segments) lysed RP-2-infected target cells while the clone, 1-2F11, that mapped only to the 0.68–0.72 segment did not. Interestingly, the type-common clone from donor 4 (4-7B1) lysed all three HSV-1 strain-infected targets, but not the RP-2-infected targets.

To confirm that the three clones that lysed RP-2 infected targets recognized VP16 and to identify the targets of the other two CTL that mapped to this region of the genome, recombinant vaccinia viruses expressing HSV-2 ORFs UL46, UL47, UL48 (VP16) and UL49 (VP22) were constructed. Two separate vaccinia virus recombinants expressing VP16 were constructed, one expressing a full length protein VP16$_{FL}$ and one expressing a C-terminally truncated protein VP16t.

The RP-2 reactive CTL clones were first tested with vac/VP16t and vac/VP16$_{FL}$ infected autologous B-LCL (Table 5) and none recognized the VP16-expressing targets. Although 3–6F9 was inactive in this experiment, an active passage of the clone lysed RP-2 infected B-LCL, but not vac/VP16-infected targets. When these same CTL clones were tested with the other vaccinia recombinants (Table 6), all five clones that mapped to this region of the genome recognized vac/UL49-infected target cells as indicated by the bold type face. The 4-7B1 clone has ceased to grow when restimulated. The number of T cells available for use in this experiment were very small so that the effector:target ratios were much less than the 10:1 starting ratio used for the other CTL clones. Thus, although the specific lysis was only 6%, it is probably a positive result, hence the use of a dotted line to draw the box. Clones that did not map to the region recognized none of these ORFs, nor did the type-common clones surveyed thus far recognize UL49.

In summary of the results presented in this section, twenty-two HSV-specific CD8$^+$ CTL were isolated from three individuals with frequently recurring genital herpes. To identify which of the more than 75 HSV proteins were recognized by the clones, they were screened for HSV type specificity, for recognition of internal virion proteins and for recognition of individual HSV proteins gB, gD, UL46, UL47, UL48 (VP16), and UL49 (VP22). The results are summarized in Table 7. Thirteen of the twenty-two clones were HSV-2 type specific and the remaining clones recognized both HSV-2 and HSV-1 proteins. 19/21 clones recognized virion proteins. 1/19 recognized gB and 1/19 recognized gD. 17/19 of the clones recognized internal virion proteins comprising the tegument and capsid regions. 14 of these 17 clones were analyzed using intertypic HSV recombinants to map the location of the gene or using individual recombinant vaccinia viruses expressing UL46, UL47, UL48 (VP16) or UL49 (VP22) proteins to identify specific protein targets. The frequency of recognition of these proteins was UL46 (0/14), UL47 (0/14), UL48 (VP16) 0/14 and UL49 (VP22) 5/14.

Experiments were also performed to determine the frequency of responses to various viral proteins using the recombinant vaccinia viruses. The results of four experiments with CD8$^+$ T cells from one individual are summarized in Table 7. Several complex targets were tested including HSV-2 mutants X12 and hr259, the NK cell target line K-562 and allogeneic B-LCL infected with X12 virus. In addition 4/6 of the recombinant vaccinia viruses were tested individually (gD2, gB2, VP16 and VP22 (UL49)) and the other two were tested by co-infecting the target cells with equal amounts of vac/UL46 and vac/UL47 viruses. The results are expressed both in terms of 1/# CD8$^+$ T cells and in terms of # CTL per 10$^6$ CD8$^+$ T cells with the upper and lower 95% confidence limits. The quality of the estimate is indicated by the chi square value because the frequencies were estimated by chi square minimization.

The results show that CTLs that recognize gD and gB epitopes are not as rare as previously thought. In experiment 1, gB-specific CTL were present in 1 of ~5,000 CD8$^+$ T cells, gD-specific CTL comprised 1 of 10,000 CD8$^+$ T cells compared with 1 in ~66,000 CD8$^+$ T cells that recognized VP16 against a background of non-specific lysis of uninfected B-LCL in 1 in ~250,000 CD8$^+$ T cells. In experiment 2, gD-specific CTL were detected at a similar level (1 in ~6,000 CD8$^+$ T cells) compared with CTL that recognized target B-LCL infected with HSV-2 mutants that preserved class I antigen presentation (X12) or expressed a limited number of HSV genes (hr259/ICP4$^-$) where 1 in ~3,000 to 1 in ~17,000 CD8$^+$ T cells recognized these two targets, respectively. These values were measured against a background of 1 in 80,000 T cells exhibiting non-specific lysis of uninfected B-LCL. In experiment 3, the number of VP16-specific CTL detected were similar to the number of Natural Killer cells, which recognize and lyse K-562 cells or non-specific T cells. Finally, in experiment 4, epitopes from VP16, UL46 or UL47 were much less represented in the CTL response in this subject while epitopes from VP22 (UL49) were recognized with frequencies comparable to those in whole virus. This suggests that VP22 is an immunodominant specificity in the human CTL response.

Accordingly, high frequencies of CD8$^+$ CTL that recognize epitopes from VP22 (encoded by UL49) have been measured. Moreover, four cloned CTL that had previously been thought to recognize epitopes in VP16 actually recognize VP22. Thus, this protein is especially useful for inducing or enhancing a CTL response in HSV$^+$ subjects.

TABLE 1

Identification of two CTL clones
that recognize HSV glycoproteins D and B

| EFFECTOR | TARGET RATIO | % SPECIFIC RELEASE | | | | |
|---|---|---|---|---|---|---|
| | | uninf | HSV | vac/WR | vac/gD2 | vac/gB2 |
| 1-1H6 | 10:1 | 1 | 23 | 8 | 64 | 6 |
| | 5:1 | 1 | 15 | 6 | 41 | 4 |
| | 2.5:1 | 0 | 3 | 7 | 31 | 6 |
| 1-3B3 | 10:1 | −8 | 59 | 14 | 10 | 3 |
| | 5:1 | −10 | 40 | 13 | 12 | 4 |
| | 2.5:1 | −10 | 23 | 19 | 19 | 11 |
| 3-8G1 | 10:1 | 1 | 60 | 0 | 0 | 93 |
| | 2.5:1 | 0 | 54 | −1 | 0 | 87 |
| | .625:1 | −1 | 30 | −2 | −2 | 53 |
| 3-3G2 | 10:1 | 2 | 69 | 0 | 2 | −1 |
| | 2.5:1 | 8 | 71 | 0 | 0 | −2 |
| | .625:1 | 0 | 32 | 0 | −1 | −3 |
| 3-6F9 | 10:1 | 1 | 93 | 0 | 1 | −1 |
| | 2.5:1 | 2 | 87 | 0 | 1 | −1 |
| | .625:1 | 1 | 52 | −3 | 0 | −2 |
| 3-6G3 | 10:1 | 2 | 89 | 0 | 3 | 2 |
| | 2.5:1 | 0 | 74 | 1 | 2 | 2 |
| | .625:1 | 0 | 33 | −2 | 1 | −1 |

Experimental Procedure: Autologous B-LCL target cells were used as uninfected or as infected at a m.o.i. = 10 with wild-type HSV-2 (strain 333) or at a m.o.i. = 5 with the wild type vaccinia virus (vacWR) or recombinant vaccinia viruses (vac/gD2, vac/gB2) for 18 hr. The cells were loaded with $^{51}$Cr for the last 90 min. of the infection and then mixed with autologous CTL clones at the effector:target ratios indicated for 4 hr. Spontaneous $^{51}$Cr release did not exceed 15%. Positive lysis of infected target cells is indicated by boldface type.

TABLE 2

CTL clones from two donors that recognize virion proteins

| CTL clone | HLA Restriction | uninf | HSV-2 (333) 18 hr | HSV-2 (333) 3 hr | HSV-2 (333) 3 hr + DRB | HSV-2 ICP4 3 hr |
|---|---|---|---|---|---|---|
| 1-3B3 | A32 | 2 | 76 | 54 | 54 | 74 |
| 1-2A11 | A24,32 | 2 | 38 | 33 | 31 | 52 |
| 1-1G1 | B7 | 12 | 64 | 73 | 71 | 82 |
| 1-1G11 |  | 1 | 80 | 43 | 52 | 80 |
| 1-4G3 |  | 1 | 75 | — | — | 89 |
| 3-6G3 | A2 | 0 | 13 | 29 | 36 | 32 |
| 3-3G2 | B7 | 0 | 52 | 44 | 29 | 24 |
| 3-6F9 | B7 | 0 | 81 | 72 | 76 | 64 |
| 3-8G1 | A2.1 | 0 | 41 | 16 | 10 | 8 |

Experimental Procedure: Autologous B-LCL were infected at a m.o.i. = 20 with wild-type HSV-2 (strain 333) or with the HSV-2 ICP4 minus mutant strain hr259 for either 3 or 18 hr. The cells were loaded with $^{51}$Cr for the last 90 min. of the infection then mixed with autologous CTL clones at an effector:target ratio of 10:1 for 4 hr. Spontaneous $^{51}$Cr release did not exceed 13% with the exception of donor 3 cells infected for 18 hr with 333 where spontaneous release was 35%. In a subset of the cells infected for 3 hr with wild type HSV-2, viral transcription was blocked by treating the B-LCL for 30 min. prior to infection with 100 mM 5,6-dichloro-1-β-D-ribofuranosyl-benzimidazole (DRB) and the drug was maintained at this level in the cultures during $^{51}$Cr loading, all washing steps and during exposure to the CTLs. Positive lysis of infected target cells is indicated by boldface type.

TABLE 3

Mapping of the location of the HSV genes encoding the antigens recognized by HSV-specific of human CTL clones using HSV-1 × HSV-2 intertypic recombinants

| Clone | HSV-2 | RH 1G7 0.3–0.45 | RH 1G8 0.385–0.45 | RH 1G44 0.37–0.405 | RS 1G25 0.59–0.72 | RS 1G31 0.68–0.72 | R 7015 0.8–1.0 |
|---|---|---|---|---|---|---|---|
| 1-3B3 | 87 | 76 | 78 | 61 | 37 | 29 | 70 |
| 3-8G1 | 49 | 48 | 52 | 33 | 22 | 23 | 56 |
| 1-1H6 | 52 | 4 | 0 | 1 | 4 | — | 71 |
| 1-2A11 | 53 | 16 | 12 | 13 | 4 | 4 | 10 |
| 1-2D12 | 67 | 3 | 0 | 0 | 58 | 59 | 50 |
| 1-1G1 | 25 | 5 | 2 | 2 | 37 | 38 | 21 |
| 1-2H12 | 25 | 7 | 2 | 5 | 0 | 4 | 3 |
| 1-2E7 | 24 | 6 | 1 | 7 | 3 | — | 1 |
| 1-2F11 | 52 | 0 | 0 | 0 | 48 | 54 | 2 |
| 3-6F9 | 77 | 2 | 2 | 1 | 73 | — | 54 |
| 3-3G2 | 60 | 73 | 0 | 0 | 0 | 55 | 4 |
| 4-2B10 | 32 | 2 | — | — | 0 | — | 0 |
| 4-11H2 | 36 | 2 | — | — | 0 | — | 0 |
| 4-19A7 | 42 | 0 | 0 | 1 | 3 | 0 | 0 |

Experimental procedure: Autologous B-LCL were infected for 18 hr. at a m.o.i. = 20 with wild type HSV-2 (strain 333) or the intertypic recombinant viruses. The target cells were loaded with $^{51}$Cr for 90 min. then mixed with the 14 CTL clones at an effector:target ratio of 10:1. Spontaneous release from any of the targets did not exceed 20%. The two type common CTL clones, 1-3B3 and 3-8G1 were included as infectivity controls. Positive lysis of the infected target cells is indicated in boldface type.

TABLE 4

HSV-specific CTL clones that recognize epitopes in or near VP16

| | | | HSV-1 | | |
|---|---|---|---|---|---|
| clone | uninf | HSV-2 | Patton | F | KOS | RP-2 |
| 1-3B3 | 2 | 64 | 33 | 25 | 41 | 44 |
| 1-2F11 | 1 | 49 | 0 | 1 | — | 4 |
| 1-2D12 | 0 | 88 | 0 | 4 | 6 | 59 |
| 1-1G1 | 0 | 56 | 2 | 5 | 0 | 56 |
| 3-6F9 | 2 | 59 | 2 | 4 | — | 52 |
| 4-7B1 | 2 | 73 | 41 | 40 | 61 | 1 |

Experimental procedures: Autologous B-LCL were infected with a m.o.i. = 20 with HSV-2 (strain 333), three HSV-1 strains or the HSV-1 KOS × VP16-2 intertypic recombinant virus RP-2 for 18 hr. before being loaded with $^{51}$Cr and mixed with the 6 CTL clones. Positive lysis of the infected target cells is indicated by boldface type.

TABLE 5

HSV-specific CTL clones mapped with the intertypic recombinant RP-2 fail to lyse autologous B-LCL infected with vac/VP16.

| | | % Specific Release | | | | | % Spon. Rel. | | |
|---|---|---|---|---|---|---|---|---|---|
| B-LCL | Ratio | 1-3B3 | 1-1G1 | 1-2D12 | 3-6F9 | 4-7B1 | 1 | 3 | 4 |
| uninf | 10:1 | −2 | 2 | 2 | 2 | 2 | 11 | 14 | 9 |
| | 2.5:1 | 0 | 0 | 1 | −4 | 0 | | | |
| | .625:1 | 1 | −3 | 0 | 2 | 0 | | | |
| 333-vhs B | 10:1 | 99 | 44 | 67 | 7 | 58 | 19 | 15 | 16 |
| | 2.5:1 | 38 | 30 | 20 | 2 | 21 | | | |
| | .625:1 | 16 | 10 | 4 | 3 | 16 | | | |
| vac/VP16 | 10:1 | 7 | 3 | −5 | 1 | 10 | 24 | 20 | 17 |
| | 2.5:1 | −3 | 1 | 3 | 2 | 8 | | | |
| | .625:1 | 2 | 3 | 5 | −4 | 11 | | | |
| vac/VP16t | 10:1 | 4 | 1 | −2 | 2 | 8 | 25 | 14 | 19 |
| | 2.5:1 | −3 | −4 | 2 | 4 | 5 | | | |
| | .625:1 | 1 | 0 | 5 | 3 | 1 | | | |

Experimental procedures: Autologous B-LCL were infected with the recombinant vaccinia viruses at an m.o.i. = 5 and the 333-vhsB virus with a m.o.i. = 10 for 18 h. Positive lysis of infected target cells is indicated by boldface type.

TABLE 6

Identification of UL49 as a prominent target of the CTL response

| | | % SPECIFIC RELEASE | | | | | | | | | |
|---|---|---|---|---|---|---|---|---|---|---|---|
| TARGET JC B-LCL | RATIO | 1-3B3 | 1-2F11 | 1-2E7 | 1-1G1 | 1-2D12 | % Spon. release | 1-2H12 | 1-1G11 | 1-2A11 | % Spon. release |
| uninf | 10:1 | 0 | −1 | −1 | −1 | −1 | 9 | 0 | 0 | −1 | 10 |
| | 2.5:1 | 0 | 0 | 0 | −1 | −1 | | 0 | −1 | −1 | |
| | .625:1 | −1 | −1 | −2 | −1 | −1 | | 0 | −1 | 0 | |
| 333-vhsB | 10:1 | 49 | 45 | 12 | 60 | 32 | 12 | 17 | 46 | 36 | 14 |
| | 2.5:1 | 36 | 31 | 10 | 39 | 15 | | 12 | 31 | 21 | |
| | .625:1 | 15 | 15 | 7 | 18 | 5 | | 7 | 17 | 8 | |
| vac/UL46 | 10:1 | 1 | 0 | 1 | 0 | 0 | | 1 | 1 | 0 | 11 |
| | 2.5:1 | 1 | 0 | 0 | 0 | 1 | | 0 | 0 | −1 | |
| | .625:1 | 1 | 1 | 0 | 0 | 1 | | 0 | −1 | −1 | |
| vac/UL47 | 10:1 | 1 | 0 | 1 | 1 | 0 | 9 | −2 | −2 | −1 | 12 |
| | 2.5:1 | 1 | 1 | 0 | 0 | 0 | | −1 | −2 | −2 | |
| | .625:1 | 0 | 0 | 0 | 0 | −1 | | −2 | −3 | −2 | |

TABLE 6-continued

Identification of UL49 as a prominent target of the CTL response

| | | | | | | | | | | | |
|---|---|---|---|---|---|---|---|---|---|---|---|
| vac/UL49 | 10:1 | 0 | 56 | 0 | 64 | 50 | 10 | 0 | 1 | 0 | 9 |
| | 2.5:1 | −1 | 38 | 1 | 45 | 23 | | 0 | 0 | 0 | |
| | .625:1 | −1 | 19 | 0 | 19 | 9 | | 1 | 0 | 1 | |

| | | % SPECIFIC RELEASE | | | | | % Spon. release | |
|---|---|---|---|---|---|---|---|---|
| | | GS B-LCL | | NIH B-LCL | | | | |
| TARGET | RATIO | 3-6G3 | 3-6F9 | 4-1F11 | 4-1B7 | 4-7B1 | GS | NIH |
| uninf | 10:1 | 0 | −1 | 0 | −1 | 0 | 9 | 6 |
| | 2.5:1 | 0 | 0 | −1 | −1 | 0 | | |
| | .625:1 | 0 | 0 | −1 | 0 | 0 | | |
| 333-vhs B | 10:1 | 27 | 60 | 20 | 54 | | 15 | 11 |
| | 2.5:1 | 13 | 50 | 17 | 46 | | | |
| | .625:1 | 4 | 24 | 12 | 28 | | | |
| vac/UL46 | 10:1 | 1 | 0 | 0 | 0 | | 10 | 10 |
| | 2.5:1 | 1 | 0 | 0 | 0 | | | |
| | .625:1 | 1 | 0 | 0 | 0 | | | |
| vac/UL47 | 10:1 | −1 | 0 | −1 | 0 | | 11 | 11 |
| | 2.5:1 | −1 | 0 | −2 | −1 | | | |
| | .625:1 | −2 | 0 | −2 | −2 | | | |
| vac/UL49 | 10:1 | −1 | 58 | 0 | 1 | 6 | 15 | 12 |
| | 2.5:1 | −1 | 44 | 1 | 0 | 2 | | |
| | .625:1 | −2 | 19 | 0 | −1 | 1 | | |

Experimental procedures: The CTL clones were restimulated as described in Table 4. Autologous B-LCL were infected with the recombinant vaccinia viruses at an m.o.i. = 5 and the 333-vhsB virus with a m.o.i. = 10 for 18 h. The $^{51}$Cr release assay is described in Table 2. Positive lysis of infected target cells is indicated by boldface type.

TABLE 7

Summary of HSV-specific CD8+ CTL Clone Characterization

| | HLA | type | | | Intertypic | Vaccinia Recombinant | | | | | |
|---|---|---|---|---|---|---|---|---|---|---|---|
| Clone | restriction | specific | DRB | ICP4− | map | VP16 | UL46 | UL47 | UL49 | Antigen | Notes |
| 1-1H6.5 | B7 | + | − | ± | .8–1 | (−) | (−) | (−) | (−) | gD2 | |
| 1-3B3.4 | A32 | − | + | + | nd | − | − | − | − | | |
| 1-2H12.5 | B7 | + | + | | none | − | − | − | − | | |
| 1-2E7.7 | B7 | + | − | | none | − | − | − | − | | |
| 1-2C1 | B7 or Cw7 | + | ++ | nd | nd | nd | nd | nd | nd | | lost spec. |
| 1-2F11 | B7 | + | + | | .68–.72 | − | − | − | + | UL49 | |
| 1-2D12 | B7 | + | + | | .59–1 | − | − | − | + | UL49 | |
| 1-2A11 | | + | + | + | none | − | − | − | − | | |
| 1-1G1 | B7 | + | + | | .59–1 | − | − | − | + | UL49 | |
| 1-1G11 | | − | + | | nd | − | − | − | − | | |
| 1-4G3 | | − | nd | + | nd | nd | nd | nd | nd | | lost clone |
| 3-6G3 | A2 | − | + | + | nd | − | − | − | − | | |
| 3-6F9 | B7 | + | + | + | .59–1 | − | − | − | + | UL49 | |
| 3-8G1 | A2 | − | − | − | nd | (−) | (−) | (−) | (−) | gB | |
| 3-3G2 | B7 | + | ± | ± | .3–.45 | − | (−) | (−) | (−) | | |
| 4-1B7 | | − | nd | + | nd | − | − | − | − | | |
| 4-1F11 | | − | nd | + | nd | − | − | − | − | | |
| 4-2B10 | | + | nd | + | none | (−) | (−) | (−) | (−) | | |
| 4-3G1 | | − | nd | + | nd | nt | nt | nt | nt | | |
| 4-7B1 | | − | nd | ± | nd | − | (−) | (−) | + | UL49 | |
| 4-11H2 | | + | nd | + | none | (−) | (−) | (−) | (−) | | |
| 4-19A7 | not Cw7 | + | | | none | (−) | (−) | (−) | (−) | | |
| Total clones: | 22 | 13 | 11/13 | 13/14 | | 0/19 | 0/19 | 0/19 | 5/19 | | | nd, not done; nt, not yet tested, (−), inferred from data, not tested directly.

TABLE 8

Summary of Limiting Dilution Analyses

| LDA # | | JC uninf | allo HSV | K-562 | X12 | ICP4− | VP16 | gD2 | gB2 | UL49 | UL46/47 |
|---|---|---|---|---|---|---|---|---|---|---|---|
| 1 | CTLp 1/x | 250,719 | | | | | 65,821 | 10,145 | 4,604 | | |
|   | Upper SD | 874,688 | | | | | 132,294 | 15,801 | 7,883 | | |
|   | Lower SD | 71,865 | | | | | 32,749 | 6,514 | 2,689 | | |
|   | chisquare | 41.57 | | | | | 9.46 | 7.50 | 9.67 | | |
|   | CTLp/$10^6$ | 4.0 | | | | | 15.2 | 98.6 | 217.2 | | |
|   | Upper Limit | 1.1 | | | | | 7.6 | 63.3 | 126.9 | | |
|   | Lower Limit | 13.9 | | | | | 30.5 | 153.5 | 371.9 | | |
| 2 | CTLp 1/x | 81,202 | | | 2,872 | 17,305 | | 6,262 | | | |
|   | Upper SD | 320,048 | | | 4,781 | 36,247 | | 10,754 | | | |
|   | Lower SD | 20,602 | | | 1,725 | 8,262 | | 3,646 | | | |
|   | chisquare | 6.55 | | | 7.68 | 3.54 | | −17.51 | | | |
|   | CTLp/$10^6$ | 12.3 | | | 348.2 | 57.0 | | 159.7 | | | |
|   | Upper Limit | 3.1 | | | 209.2 | 27.6 | | 93.0 | | | |
|   | Lower Limit | 48.5 | | | 579.7 | 121.0 | | 274.2 | | | |
| 3 | CTLp/1x | | 144,120 | 100,445 | 65,512 | | 104,469 | | | | |
|   | Upper SD | | 480,952 | 278,040 | 151,714 | | 294,614 | | | | |
|   | Lower SD | | 43,186 | 36,287 | 28,289 | | 37,045 | | | | |
|   | chisquare | | 9.16 | 7.02 | 10.52 | | 9.58 | | | | |
|   | CTLp/$10^6$ | | 6.9 | 10.0 | 15.3 | | 9.6 | | | | |
|   | Upper Limit | | 2.1 | 3.6 | 6.6 | | 3.4 | | | | |
|   | Lower Limit | | 23.2 | 27.6 | 35.3 | | 27.0 | | | | |
| 4 | CTLp 1/x | | 247,142 | | 22,499 | | | | | 16,269 | 151,342 |
|   | Upper SD | | 1,178,018 | | 39,510 | | | | | 27,142 | 527,450 |
|   | Lower SD | | 51,849 | | 12,812 | | | | | 9,752 | 43,425 |
|   | chisquare | | 5.23 | | 2.34 | | | | | 13.10 | 2.52 |
|   | CTLp/$10^6$ | | 4.0 | | 44.4 | | | | | 61.5 | 6.6 |
|   | Upper Limit | | 0.8 | | 25.3 | | | | | 36.8 | 1.9 |
|   | Lower Limit | | 19.3 | | 78.1 | | | | | 102.5 | 23.0 |

EXAMPLE 2

This example shows the ability of VP22 to induce a CTL response in mice. The vaccines used in the experiment included a recombinant vaccinia virus, vac/UL49F (which expresses the full length VP22 protein in infected cells), and a DNA vaccine, pCMV/UL49, including the UL49 ORF driven by the CMV immediate early promoter. A vac/gB2 and pCMV/gB2 were used as positive controls.

In particular, 16 female strain C57BL/6 mice (H-$2^b$) (from Charles River), 6 weeks of age, were divided into four groups of four animals each and immunized as shown in Table 9. C57BL/6 mice were used based on their ability to recognize an HSV gB2 epitope (Hanke et al., *J. Virol.* (1991) 65:1177–1186).

TABLE 9

Experimental Design

| Group # | # of Animals | Antigen | Dose | Injection Volume | Route |
|---|---|---|---|---|---|
| 1 | 4 | vac/gB | $10^7$ pfu | 50 ml | IP* |
| 2 | 4 | pCMVgB DNA | 2 × 50 mg | | Anterior tibialis |
| 3 | 4 | pCMVUL49 DNA | 2 × 50 mg | 50 μl | Anterior tibialis |
| 4 | 4 | vac/UL49 | $10^7$ pfu | 50 ml | IP* |

*IP = intraperitoneal

All antigens were diluted or reconstituted in Dulbecco's Ca$^{++}$Mg$^{++}$ free PBS. The immunization schedule included one immunization for animals receiving vaccinia (groups 1 and 4) and one or two immunizations with DNA. One month after the first immunization, two animals in each group were boosted. The other two animals were used for CTL assays one week later (at week 5) while the boosted animals were used for repeat assays two weeks after the booster immunization.

Spleens were harvested and spleenocytes restimulated as follows. Harvested spleens were dispersed against a screen to a single cell suspension in wash media (a 1:1 mixture of RPMI and α-MEM with the addition of 10% heat-inactivated fetal calf serum, $2\times10^{-5}$ M 2-mercaptoethanol, and 50 μg/ml gentamycin). The cells were then plated into a 24-well tissue culture plate at a density of $5\times10^6$ cells per well. Antigen presenting cells (APC) were prepared by pulsing $3\times10^6$ spleenocytes with 10 μM gB2 peptide or infecting the cells with vac/UL49 virus at an m.o.i.=10 for 1 hr. VP22 protein was also used to restimulate the groups 3 and 4 in a repeat assay at a concentration of 0.0125 mg/ml 2% Rat T-stim supplement without Con A (Collaborative Biomedical Products, Bedford, Mass.) was added to the media for restimulation. The media was changed on day 3. After 1 week of restimulation, the CTL were dispensed into 96-well plates at various E:T ratios for incubation with targets, as indicated in Table 10.

MC57 (H$2^b$) cells were either pulsed with gB2 peptide for 1.5 hours (concurrent with $^{51}$Cr loading), infected with vac/UL49 for 16 hours at an m.o.i.=10, or infected with vaccinia wild-type (vac/Wr) at an m.o.i.=10 as a negative control and to serve as cold targets. Cold targets were added at a 30:1 ratio with $^{51}$Cr-loaded target cells. In addition, MHC-mismatched SVBalb cells (H2$^d$) were used as allogeneic targets and were either peptide-pulsed or infected with vac/UL49. CTL targets were co-cultured at the indicated E:T ratio for 4 hrs. in a total volume of 200 μl before 50 μl of supernatant was harvested and dispensed into Luma plates containing dry scintillant for counting.

After a single immunization, there was strong positive lysis in the vac/gB immunized mice (group 1) and in the DNA immunized mice (group 2). Neither the UL49 DNA group (group 3) or the vac/UL49 group (group 4) showed detectible specific lysis of the vac/UL49 infected.

TABLE 10

$^{51}$Cr Release

| Vaccine Group Restim. | TARGET RATIO | % SPECIFIC RELEASE | | | | | | | C:H Ratio |
|---|---|---|---|---|---|---|---|---|---|
| | | AUTO (MC57) | | | | | Allo (SVBalb) | | |
| | | Uninf | gB2 Pep. | vac/UL49 + cold | Wr + Cold | Wr − Cold | gB2 Pep. | vac/UL49 + Cold | |
| 1 | 50 | 14 | 77 | | | | 24 | | |
| Vac/gB | 13 | 5 | 48 | 11 | | | | | |
| gB2 pep, Vac/gB2 | 3 | −1 | 19 | | | | 4 | | |
| % Spon. Release | | 22 | 21 | | | | 17 | | |
| 2 | 50 | 3 | 40 | | 4 | | | | |
| pCMVgB DNA | 13 | 1 | 14 | | 1 | | | | |
| gB2 pep. | 3 | −2 | 4 | | | | | | |
| % Spon. Release | | 23 | 21 | | | | 18 | | |
| 3 | 50 | −3 | | −8 | 24 | 0 | | 0 | |
| pCMVUL49 DNA | 13 | −6 | | −10 | 9 | 0 | | −3 | 30:1 |
| Vac/UL49 | 3 | −7 | | −10 | 5 | 1 | | −3 | |
| % Spon. Release | | 26 | | 14 | 20 | 24 | | 26 | |
| 4 | 50 | 0 | | 11 | 50 | 86 | | 10 | |
| vac/UL49 | 12 | −1 | | 3 | 18 | 58 | | 2 | 30:1 |
| Vac/UL49 | 3 | −6 | | 0 | 5 | 31 | | 0 | |
| % Spon. Release | | 26 | | 14 | 20 | 24 | | 26 | |

The above experiment was repeated with the exception that VP22 protein was used as an additional means of restimulating the spleenocytes (groups 3b and 4b, Table 11). The animals in groups 2 and 3 had received booster immunizations.

The experiment showed that gB2-specific CTL were induced in each of the gB2-immunized groups (groups 1–2). There were no CTL induced in any of the UL49 groups in this experiment (groups 3 and 4) whether restimulated with virus or VP22 protein.

TABLE 11

$^{51}$Cr Release

| Vaccine Group Restim. | TARGET RATIO | % SPECIFIC RELEASE | | | | | | C:H Ratio |
|---|---|---|---|---|---|---|---|---|
| | | AUTO (MC57) | | | | Allo (SVBalb) | | |
| | | Uninf | gB2 Pep. | vac/UL49 + Cold | vac/UL49 − cold | gB2 Pep. | vac/UL49 | |
| 1 | 50 | 0 | 61 | | | 1 | | |
| Vac/gB | 13 | −3 | 49 | | | 1 | | |
| gB pep. | 3 | −3 | 29 | | | 0 | | |
| % Spon. Release | | 17 | 14 | | | 9 | | |
| 2 | 50 | 3 | 61 | | | −1 | | |

TABLE 11-continued

| Vaccine Group | TARGET | | | % SPECIFIC RELEASE | | | | C:H |
|---|---|---|---|---|---|---|---|---|
| | | | | AUTO (MC57) | | | Allo (SVBalb) | |
| Restim. | RATIO | Uninf | gB2 Pep. | vac/UL49 + Cold | vac/UL49 − cold | gB2 Pep. | vac/UL49 | Ratio |
| pCMVgB DNA | 13 | 3 | 49 | | | −1 | | |
| gB pep. | 3 | −1 | 29 | | | −2 | | |
| % Spon. Release | | 16 | 14 | | | 10 | | |
| 3a | 52 | 0 | | −3 | 5 | | 9 | |
| pCMVUL49 DNA | 13 | −2 | | −2 | 5 | | 5 | 30:1 |
| vac/UL49 | 3 | −3 | | −3 | 8 | | 6 | |
| % Spon. Release | | 16 | | 13 | 13 | | 18 | |
| 4a | 50 | 1 | | 16 | 49 | | 11 | |
| vac/UL49 | 13 | −1 | | 7 | 22 | | 5 | |
| vac/UL49 | 3 | 0 | | 3 | 12 | | 2 | 30:1 |
| % Spon. Release | | 16 | | 13 | 13 | | 18 | |
| 3b | 50 | −1 | | −2 | 2 | | 1 | |
| pCMVUL49 DNA | 13 | −2 | | −4 | 0 | | 3 | 30:1 |
| VP22 protein | 3 | −3 | | −2 | 2 | | 0 | |
| % Spon. Release | | 18 | | 13 | 13 | | 20 | |
| 4b | 50 | 2 | | −3 | 3 | | 6 | |
| vac/UL49 | 13 | 2 | | −1 | 3 | | 5 | |
| VP22 protein | 3 | −1 | | −1 | 0 | | 3 | 30:1 |
| % Spon. Release | | 18 | | 13 | 13 | | 20 | |

The above experiments were repeated to assess the ability of two additional mouse strains, Balb/c and C3H, to recognize a CTL epitope in VP22. 16 mice (from Charles River), 6 weeks of age, were divided into four groups of four animals each and immunized as shown in Table 12. Eight mice were of strain Balb/c (H-2$^d$) and eight mice were strain C3H (H-2$^k$). The immunization schedule was as in the previous experiment.

TABLE 12

Experimental Design, Experiment #2

| Group # | # of Animals | Strain | Antigen | Dose | Injection Volume | Route |
|---|---|---|---|---|---|---|
| 1 | 4 | Balb/c | vac/UL49 | 10$^7$ pfu | 50 ml | IP* |
| 2 | 4 | Balb/c | pCMVUL49 DNA | 2 × 50 mg | 50 ml | Anterior tibialis |
| 3 | 4 | C3H | vac/UL49 | 10$^7$ pfu | 50 ml | IP* |
| 4 | 4 | C3H | pCMVUL49 DNA | 2 × 50 mg | 50 ml | Anterior tibialis |

*IP = intraperitoneal $^{51}$Cr release studies were conducted as above with the addition of the two mouse strains, as shown in Table 13. While neither the vaccinia or the DNA vaccines induced VP22-specific CTL in C3H mice (groups 3 and 4), CTL were induced in the Balb/c mice (groups 1 and 2) by both the recombinant vaccinia and DNA vaccines indicating that there is a significant epitope in VP22 in this mouse strain.

TABLE 13

| Vaccine Group | | $^{51}$Cr Release | | | | | |
|---|---|---|---|---|---|---|---|
| | | % SPECIFIC RELEASE | | | | | |
| strain Restim. | TARGET RATIO | Uninf | X12 | vac/UL49 − Cold | vac/UL49 + Cold | ALLO X12 | C:H Ratio |
| 1 | 50 | 8 | 13 | 47 | 42 | −3 | |
| Vac/UL49 | 12 | 2 | 7 | 51 | 35 | −7 | 30:1 |
| Balb/C | 3 | −4 | 8 | 42 | 19 | −11 | |
| Vac/UL49 | | 11 | 33 | 11 | | 32 | |
| % Spon. Release | | | | | 11 | | |

TABLE 13-continued

| Vaccine Group | | $^{51}$Cr Release | | | | | |
|---|---|---|---|---|---|---|---|
| | | % SPECIFIC RELEASE | | | | | |
| strain Restim. | TARGET RATIO | Uninf | X12 | vac/UL49 − Cold | vac/UL49 + Cold | ALLO X12 | C:H Ratio |
| 2 | 50 | −1 | −3 | 35 | | −11 | |
| pCMVUL49 DNA | 13 | −1 | 4 | 16 | 22 | −2 | 30:1 |
| Balb/C | 3 | −1 | 1 | 5 | 13 | −6 | |
| Vac/UL49 | | 11 | 33 | 11 | 3 | 32 | |
| % Spon. Release | | | | | 14 | | |
| 3 | 50 | 20 | 10 | 12 | 4 | 28 | |
| vac/UL49 | 12 | 14 | 1 | 15 | 5 | 24 | |
| C3H | 3 | 5 | −3 | 14 | 6 | 13 | 30:1 |
| Vac/UL49 | | | | | | | |
| % Spon. Release | | 12 | 28 | 14 | 14 | 33 | |
| 4 | 50 | 19 | 1 | 26 | 11 | 19 | |
| pCMVUL49 DNA | 12 | 9 | 1 | 9 | 7 | 12 | |
| C3H | 3 | 4 | 4 | 1 | 3 | 9 | 30:1 |
| Vac/UL49 | | | | | | | |
| % Spon. Release | | 12 | 28 | 14 | 14 | 33 | |

The experiment was repeated, as shown in Table 14. The cytotoxic activity to VP22 in the recombinant vaccinia group proved to be durable, while cytotoxicity was not boosted by a second immunization with the DNA vaccine. An epitope to VP22 was still not apparent in C3H mice after a boosting vaccination.

TABLE 14

| Vaccine Group | | $^{51}$Cr Release | | | | | |
|---|---|---|---|---|---|---|---|
| | | % SPECIFIC RELEASE | | | | | |
| strain Restim. | TARGET RATIO | Uninf | vhs b | vac/UL49 − Cold | vac/UL49 + Cold | ALLO vhs b | C:H Ratio |
| 1 | 51 | 0 | −12 | 60 | | −3 | |
| Vac/UL49 | 13 | −3 | −13 | 33 | 36 | −6 | 30:1 |
| Balb/C | 3 | −3 | −11 | 10 | 13 | −3 | |
| Vac/UL49F | | 12 | 27 | 35 | 7 | 18 | |
| % Spon. Release | | | | | 33 | | |
| 2 | 50 | −1 | −9 | 9 | 6 | −4 | |
| pCMVUL49 DNA | 13 | 0 | −4 | −2 | −1 | 0 | 30:1 |
| Balb/C | 3 | 1 | −2 | −5 | 3 | 1 | |
| Vac/UL49F | | | | | | | |
| % Spon. Release | | 12 | 27 | 35 | 33 | 18 | |
| 3 | 50 | −10 | −1 | 10 | 4 | 22 | |
| vac/UL49 | 13 | −10 | −3 | 5 | 1 | 7 | |
| C3H | 3 | −8 | −2 | 7 | 1 | 1 | 30:1 |
| Vac/UL49F | | | | | | | |
| % Spon. Release | | 13 | 18 | 30 | 24 | 31 | |
| 4 | 50 | −4 | −4 | 6 | 3 | 4 | |
| pCMVUL49 DNA | 13 | −1 | −1 | 6 | −2 | 3 | |
| C3H | 3 | 0 | 1 | −2 | 2 | 5 | 30:1 |
| Vac/UL49F | | | | | | | |
| % Spon. Release | | 13 | 18 | 30 | 24 | 31 | |

Thus, vaccine compositions including HSV VP22 polypeptides and methods of using the same are disclosed. Although preferred embodiments of the subject invention have been described in some detail, it is understood that obvious variations can be made without departing from the spirit and the scope of the invention as defined by the appended claims.

We claim:

1. A composition comprising an isolated polypeptide, and a pharmaceutically acceptable excipient, wherein said polypeptide shares at least one antigenic determinant with the HSV VP22 polypeptide of SEQ ID NO: 2, and has at least 90% sequence identity with the sequence of SEQ ID NO: 2.

2. The composition of claim 1, wherein the polypeptide is from HSV type 2 (HSV-2).

3. The composition of claim 1, further comprising an adjuvant.

4. The composition of claim 1, wherein said VP22 polypeptide has the amino acid sequence of SEQ ID NO:2.

5. The composition of claim 1, further comprising HSV VP16, or a truncated derivative thereof comprising amino acids 1–416 of the full-length sequence.

6. The composition of claim 5, wherein the VP16 is from HSV-1.

7. The composition of claim 5, wherein the VP16 is from HSV-2.

8. The composition of claim 1 further comprising a HSV glycoprotein polypeptide.

9. The composition of claim 8, wherein the glycoprotein is gB from HSV-1 and lacks all or a portion of the transmembrane domain and/or the cytoplasmic domain.

10. The composition of claim 8, wherein the glycoprotein is gB from HSV-2 and lacks all or a portion of the transmembrane domain and/or the cytoplasmic domain.

11. The composition of claim 8, wherein the glycoprotein is gD from HSV-1 and lacks all or a portion of the transmembrane domain and/or the cytoplasmic domain.

12. The composition of claim 8, wherein the glycoprotein is gD from HSV-2 and lacks all or a portion of the transmembrane domain and/or the cytoplasmic domain.

13. A method of producing a composition, the method comprising:
   (a) providing an isolated polypeptide, wherein said polypeptide shares at least one antigenic determinant with the HSV VP22 polypeptide of SEQ ID NO: 2, and has at least 90% sequence identity with the sequence of SEQ ID NO: 2; and
   (b) formulating the polypeptide with a pharmaceutically acceptable excipient.

14. The method of claim 13, wherein the polypeptide is from HSV type 2 (HSV-2).

15. The method of claim 13, further comprising adding an adjuvant.

16. The method of claim 13, wherein said VP22 polypeptide has the amino acid sequence of SEQ ID NO:2.

17. The method of claim 13, wherein the composition further comprises HSV VP16, or a truncated derivative thereof comprising amino acids 1–416 of the full-length sequence.

18. The composition of claim 17, wherein the VP16 is from HSV-1.

19. The composition of claim 17, wherein the VP16 is from HSV-2.

20. The method of claim 13, wherein the composition further comprises a HSV glycoprotein polypeptide.

21. The method of claim 20, wherein the glycoprotein is gB from HSV-1 and lacks all or a portion of the transmembrane domain and/or the cytoplasmic domain.

22. The method of claim 20, wherein the glycoprotein is gB from HSV-2 and lacks all or a portion of the transmembrane domain and/or the cytoplasmic domain.

23. The method of claim 20, wherein the glycoprotein is gD from HSV-1 and lacks all or a portion of the transmembrane domain and/or the cytoplasmic domain.

24. The method of claim 20, wherein the glycoprotein is gD from HSV-2 and lacks all or a portion of the transmembrane domain and/or the cytoplasmic domain.

* * * * *